(12) United States Patent
Zhang et al.

(10) Patent No.: US 11,782,012 B2
(45) Date of Patent: Oct. 10, 2023

(54) FLUID ANALYZER FOR MEASURING MAGNESIUM IONS AND METHOD OF CALIBRATING POTENTIOMETRIC MAGNESIUM ION SENSOR THEREIN

(71) Applicant: Siemens Healthcare Diagnostics Inc., Tarrytown, NY (US)

(72) Inventors: Wei Zhang, Needham, MA (US); Brian Holman, Medfield, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 18/061,128

(22) Filed: Dec. 2, 2022

(65) Prior Publication Data

US 2023/0104001 A1 Apr. 6, 2023

Related U.S. Application Data

(60) Continuation of application No. 16/924,898, filed on Jul. 9, 2020, now Pat. No. 11,549,905, which is a
(Continued)

(51) Int. Cl.
*G01N 27/333* (2006.01)
*G01N 33/84* (2006.01)
(Continued)

(52) U.S. Cl.
CPC .............. *G01N 27/333* (2013.01); *C12Q 1/25* (2013.01); *G01N 27/301* (2013.01);
(Continued)

(58) Field of Classification Search
CPC .............. G01N 33/4915; G01N 27/301; G01N 27/333; G01N 27/4163
See application file for complete search history.

(56) References Cited

U.S. PATENT DOCUMENTS

| 3,960,497 A | 6/1976 | Acord |
| 4,218,746 A | 8/1980 | Koshiishi |
(Continued)

FOREIGN PATENT DOCUMENTS

| CA | 2458195 A1 | 3/2003 |
| JP | H01244356 A | 9/1989 |
(Continued)

OTHER PUBLICATIONS

European Office Action of European Patent Application No. 16852572.3 dated Sep. 27, 2018.
(Continued)

*Primary Examiner* — Caitlyn Mingyun Sun

(57) ABSTRACT

A fluid analyzer for analyzing fluid samples comprising one or more analytes and a method of calibrating such. The fluid analyzer includes a control system to control at least one automated valve to pass at least three calibration reagents through a fluid channel to a secondary ion selective electrode, a primary ion selective electrode, and a reference electrode, and determine calibration information using calibration logic from signals generated by a meter, control the at least one automated valve to selectively pass different subsets of the at least three calibration reagents through the fluid channel to the secondary ion selective electrode, the primary ion selective electrode, and the reference electrode, and determine re-calibration information using the signals generated by the meter and at least one of the calibration information and re-calibration logic.

10 Claims, 10 Drawing Sheets

Related U.S. Application Data division of application No. 15/762,892, filed as application No. PCT/US2016/054385 on Sep. 29, 2016, now abandoned.

(60) Provisional application No. 62/235,006, filed on Sep. 30, 2015.

(51) Int. Cl.
  *C12Q 1/25* (2006.01)
  *G01N 27/416* (2006.01)
  *G01N 33/50* (2006.01)
  *G01N 33/49* (2006.01)
  *G01N 27/30* (2006.01)

(52) U.S. Cl.
  CPC ..... *G01N 27/4163* (2013.01); *G01N 33/4915* (2013.01); *G01N 33/50* (2013.01); *G01N 33/84* (2013.01)

(56) References Cited

U.S. PATENT DOCUMENTS

| | | | | |
|---|---|---|---|---|
| 5,580,441 | A * | 12/1996 | Amemiya | G01N 27/4163 205/789.5 |
| 6,438,501 | B1 * | 8/2002 | Szecsody | G01N 27/4165 702/50 |
| 10,139,362 | B2 | 11/2018 | Ohgami | |
| 2003/0062262 | A1 | 4/2003 | Mansouri et al. | |
| 2009/0018426 | A1 | 1/2009 | Markle et al. | |
| 2011/0201121 | A1 | 8/2011 | Kaartinen | |
| 2012/0261260 | A1 * | 10/2012 | Li | G01N 27/333 204/416 |
| 2014/0132274 | A1 | 5/2014 | Freeman et al. | |

FOREIGN PATENT DOCUMENTS

| | | |
|---|---|---|
| JP | H07167818 A | 7/1995 |
| JP | 2006504936 A | 2/2006 |
| JP | 2008256725 A | 10/2008 |
| WO | 2004040284 A1 | 5/2004 |
| WO | 2014006406 A1 | 1/2014 |

OTHER PUBLICATIONS

International Search Report and Written Opinion of International Application No. PCT/US2016/054385 dated Dec. 8, 2016.

Eugster et al.,"Characterization Procedure for Ion-Selective Electrode Assays of Magnesium Activity in Aqueous Solutions of Physiological Composition", 1993, Clinical Chemistry, vol. 23, No. 5, pp. 855-859.

European Office Action of European Patent Application No. 16852572.3 dated Jan. 31, 2022.

* cited by examiner

FLUID ANALYZER FOR MEASURING MAGNESIUM IONS AND METHOD OF CALIBRATING POTENTIOMETRIC MAGNESIUM ION SENSOR THEREIN

CROSS REFERENCE TO RELATED APPLICATIONS/INCORPORATION BY REFERENCE STATEMENT

The subject application is a continuation of U.S. Ser. No. 16/924,898, filed Jul. 9, 2020; which is a divisional of U.S. Ser. No. 15/762,892, filed Mar. 23, 2018, now abandoned; which is a US national stage application filed under 35 USC § 371 of International Application No. PCT/US2016/054385, filed Sep. 29, 2016; which claims benefit under 35 USC § 119(e) of U.S. Provisional Application No. 62/235,006, filed Sep. 30, 2015. The entire contents of the above-referenced patent applications are hereby expressly incorporated herein by reference.

BACKGROUND

Magnesium assays are increasingly being requested in hospitals and clinical research institutions. A robust magnesium ion sensor capable of detecting a biological active portion of ionized magnesium may aid in the clinical diagnosis of patients.

Current commercial and experimental magnesium ion (Mg') sensors have issues with selectivity and/or specificity of ionized magnesium. Generally, these sensors are based on neutral ionophore-based potentiometric detection. As such, many of the sensors may need to be corrected (e.g., via algorithmic corrections) to take into account pH adjustments and/or selectivity adjustments due to other interfering species like, for example, calcium ions ($Ca^{2+}$), sodium ions ($Na^+$), and potassium ions ($K^+$).

For each type of ion, the ion selective electrodes (ISEs) making up the potentiometric sensors have a different response kinetic pattern, which causes the data to be greatly skewed if the ISEs are not calibrated to take into account the different selectivities of the ions and/or any necessary pH adjustments. Currently, the calibration of potentiometric ISEs for measuring ionized magnesium ("Mg ISEs") generally encompasses calibrating Mg ISEs with three calibration reagents which characterize the slope, intercept, and selectivity of the magnesium ions against the calcium ions. See, e.g., Eugster et al., "Characterization Procedure for Ion-Selective Electrode Assays of Magnesium Activity in Aqueous Solutions of Physiological Composition," Clin. Chem., 39, 855-859 (1993).

It is known that the selectivity coefficient is, in theory, a constant parameter for a particular electrode, reflecting the corresponding preference degree of a sensor to a primary ion over an interfering (or "secondary") ion. The selectivity coefficient is also known to mainly rely on features of a particular sensor including, for example but without limitation, the ionophore, plasticizer, and/or polymeric matrix used therein.

The Nernstian equation (I) can be used to calculate the concentration of a primary ion.

$$E = E^\circ + \frac{RT}{nz_i}\ln(a_i) \quad \text{(I)}$$

E is the measured electromotive force (EMF) of the electrode in the sample (or calibration reagent and/or quality control reagent); $E^O$ is the constant potential contributions; and $a_i$ is the activity of "I" (the primary ion), $z_i$ is the charge of the primary ion, I, and R, T, and n are: the gas constant, absolute temperature (K), and the number of moles of charger carries per mole of the species, respectively. When using the Nernstian equation (I), ion selective electrodes should achieve a sufficient selectivity pattern of the primary ion over the coexisting interfering ion with a maximum allowable error of 1%.

The selectivity coefficient for a primary ion over an interfering ion can be derived from the well-known, semi-empirical Nicolsky-Eisenman equation (II).

$$E = E^\circ + \frac{RT}{nz_i}\ln\left(a_i + \sum K_{ij}^{poc} a_j^{z_i/z_j}\right) \quad \text{(II)}$$

E is the measured electromotive force (EMF) of the electrode in the sample (or calibration reagent and/or quality control reagent); $E^O$ is the constant potential contributions; $K_{ij}^{pot}$ is the selectivity coefficient; $z_i$ and $z_j$ are the charges of the primary ion, I, and interfering ion, J; $a_i$ and $a_j$ are the activities of I and J; and R, T, and n are: the gas constant, absolute temperature (K), and the number of moles of charge carriers per mole of the species, respectively.

As is well-known in the field, $$\frac{RT}{nz_i}$$

is often referred to as the "slope" for both the Nernstian equation and the Nicolsky-Eisenman equation. Additionally, $E^O$ is often referred to as the "offset" or intercept for both the Nernstian equation and the Nicolsky-Eisenman equation. These values are interchangeable between the two equations for a single set of data, which allows for the determination of the selectivity coefficient, $K_{ij}^{pot}$, between two specific ions (i.e., a primary ion and an interfering ion) for an ion selective electrode using electric potential measurements for at least three calibration reagents and known values for the primary and interfering ions within each calibration reagent, as will be discussed in more detail herein.

As previously mentioned, when an ion selective electrode is sufficiently selective to the primary ion over the interfering ion, the contribution from the interfering ion variation in the background can be neglected up to an allowable error of 1%. However, the application of magnesium ion selective electrodes in testing the magnesium ion levels in blood, for example, is not straightforward.

Currently available potentiometric magnesium ion sensors cannot provide sufficiently high selectivity over the main secondary ion (i.e., calcium ions) due to the lack of an ionophore that is sufficiently selective of magnesium ions over competing ions. That is, the selectivity coefficient, $K^{pot}_{Mg,Ca}$, for calculating the concentration of magnesium ions in blood is unstable and varies throughout the uselife of a solid state magnesium ion sensor. The uselife generally includes an initial wetup period, a post-wetup period, and a close-to-uselife-end period. In fact, each period of a solid state magnesium ion sensor's uselife has its own apparent selectivity pattern due to many factors including, for example, the status of the internal electrolyte layer hydration, ion-flux process, membrane composition leaching, and/or sample matrix adhesion.

The methods disclosed in the prior art for calibrating potentiometric magnesium ion sensors do not take into account the unstable nature of the selectivity coefficient for calculating the concentration of magnesium ions when calcium ions are present and, as such, are only effective for around three days before they start to produce results outside of the acceptable 1% error range. This, of course, renders the long uselife (~28 days) of solid state magnesium ion sensors ineffective.

Therefore, a fluid analyzer having potentiometric magnesium ion sensors with an extended uselife capable of maintaining accurate measurements (i.e., within a 1% error range) throughout the uselife of the potentiometric magnesium ion sensors is needed.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION

Figure 1:
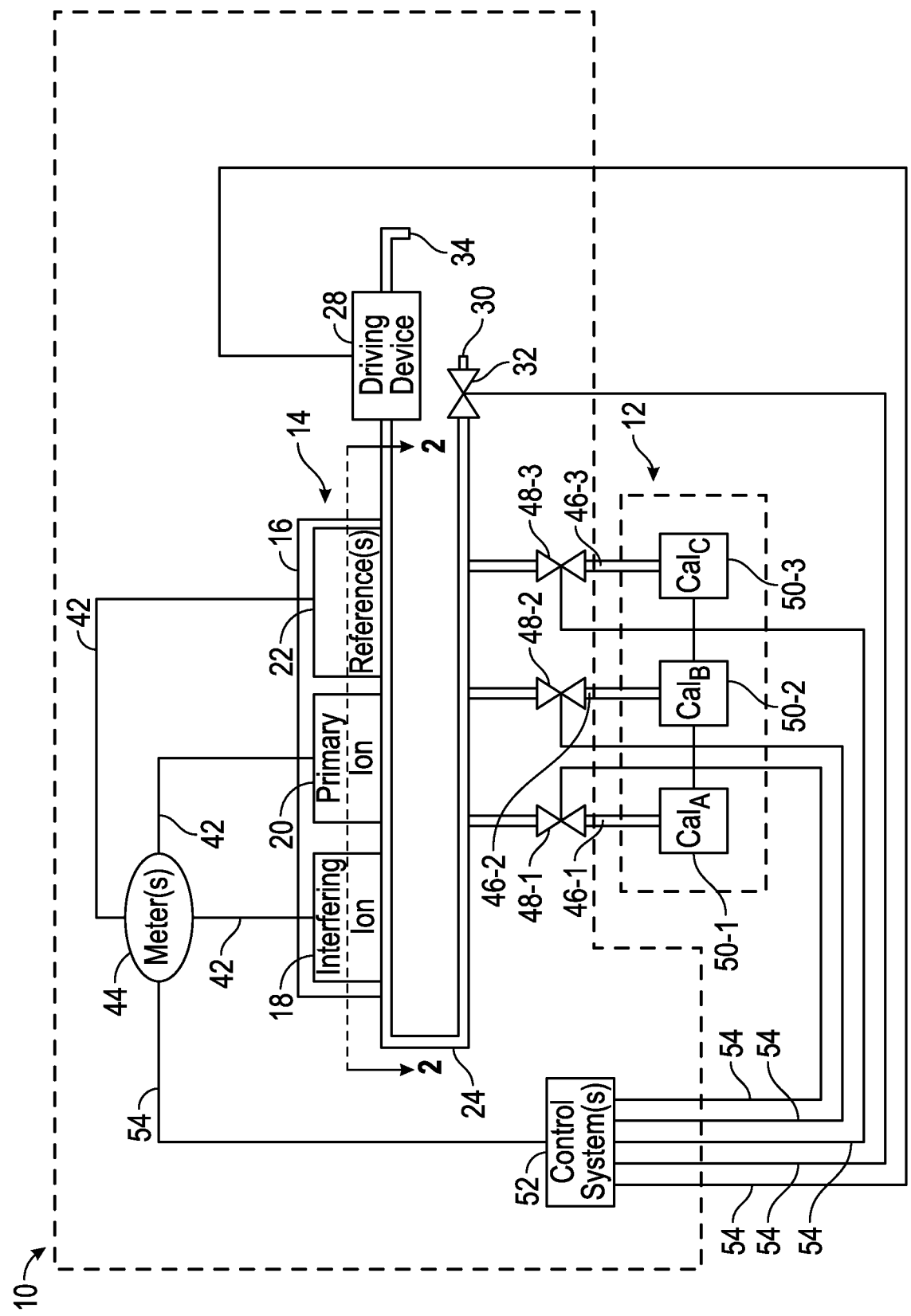
FIG. 1 illustrates a schematic diagram of an exemplary embodiment of a fluid analyzer comprising potentiometric sensors and a calibration cartridge in accordance with the present disclosure.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The disclosure is capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements. Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the fluid analyzers and/or methods disclosed and/or claimed herein can be made and executed without undue experimentation in light of the present disclosure. While the fluid analyzer and methods of this presently disclosed and/or claimed inventive concept(s) have been described in terms of preferred embodiments, it will be apparent to those of skill in the art that variations may be applied to the fluid analyzers and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more, or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20%, or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "sample" as used herein will be understood to include any type of biological sample that may be utilized in accordance with the presently disclosed and/or claimed inventive concept(s). That is, the sample may be any fluidic sample and/or sample capable of being fluidic (e.g., a biological sample mixed with a fluidic substrate). Examples of biological samples that may be utilized include, but are not limited to, whole blood or any portion thereof (i.e., plasma or serum), saliva, sputum, cerebrospinal fluid (CSF), surgical drain fluid, skin, interstitial fluid, tears, mucus, urine, swabs, combinations, and the like. It should be noted that although the present disclosure is directed towards a biological sample, one skilled in the art will appreciate that the concepts disclosed herein may be applied to any sample wherein a concentration of magnesium may be determined, and as such, the present disclosure is not limited to biological samples.

The term "wetup" as used herein will be understood to refer to the hydration process from the installation of a sensor in a fluid analyzer to a point at which a stable signal is obtained out of calibration reagents.

The term "recovery" as used herein, either alone or in connection with another term (for example but without limitation, "quality control recovery," "recovery period," and "recovery elevation"), is understood to mean the yield of an analytical process with comparison to an assigned value(s) or reference value(s).

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like.

Software may include one or more computer readable instructions that when executed by one or more components cause the component to perform a specified function. It should be understood that the algorithms described herein may be stored on one or more non-transient memory. Exemplary non-transient memory may include random access memory, read only memory, flash memory, and/or the like. Such non-transient memory may be electrically based, optically based, and/or the like.

It is to be further understood that, as used herein, the term "user" is not limited to a human being, and may comprise, a computer, a server, a website, a processor, a network interface, a human, a user terminal, a virtual computer, combinations thereof, and the like, for example.

The term "calibration information" as used herein may refer to one or more of the slope, offset, and/or selectivity coefficient of the Nernstian equation or Nicolsky-Eisenman equation determined in an initial three point calibration (i.e., "full calibration").

The term "calibration logic" as used herein refers to the program logic used by a processor within a control system to interpret data measured by one or more ion selective electrodes. In particular, the term "calibration logic" is directed to the program logic of a control system used by a processor to interpret data from a magnesium ion selective electrode for an initial three point calibration (i.e., "full calibration").

The term "re-calibration" information as used herein may refer to one or more of the slope, offset, and/or selectivity coefficient determined using the Nernstian equation or Nicolsky-Eisenman equation using information derived from any subsequent three point calibration, two point calibration, or one point calibration after an initial three point calibration.

The term "re-calibration logic" as used herein also refers to the program logic used by a processor within a control system to interpret data measured by one or more ion selective electrodes. In particular, the term "re-calibration logic" is directed to the program logic of a control system used by a processor to interpret data from a magnesium ion selective electrode for additional three point calibrations, one point calibrations, and two point calibrations (as will be defined further herein) after an initial three point calibration.

Referring now to the Figures, and in particular to FIG. 1, shown therein is an illustration of an exemplary embodiment of a fluid analyzer 10 in combination with a calibration cartridge 12. The fluid analyzer 10 generally comprises a plurality of potentiometric sensors 14. The plurality of potentiometric sensors 14 may include a housing 16 supporting and/or encompassing at least a portion of the plurality of potentiometric sensors 14.

The plurality of potentiometric sensors 14 generally comprise an interfering ion selective electrode 18, a primary ion selective electrode 20, and one or more reference electrodes 22. In one embodiment, the interfering ion selective electrode 18 is a calcium ion selective electrode generally comprising a membrane-based calcium sensor capable of quantitatively measuring a concentration of ionized calcium species within a sample solution, a quality control reagent, and/or a calibration reagent, and the primary ion selective electrode 20 is a magnesium ion selective electrode generally comprising a membrane-based magnesium sensor capable of quantitatively measuring a concentration of ionized magnesium species within a sample solution, quality control reagent, and/or calibration reagent.

Additionally, the plurality of potentiometric sensors 14 may comprise one or more additional electrodes (not pictured) for sensing other species within a sample solution, quality control reagent, and/or calibration reagent. For example, the plurality of potentiometric sensors 14 may include ion selective electrodes for sensing other species including, but not limited to, potassium ions ($K^+$), sodium ions ($Na^+$), bicarbonate ions ($HCO_3^-$), and/or pH levels. In one embodiment, the one or more reference electrodes 22 are downstream from the interfering ion selective electrode 18, the primary ion selective electrode 20, and/or the additional electrodes (not pictured).

Figure 2:
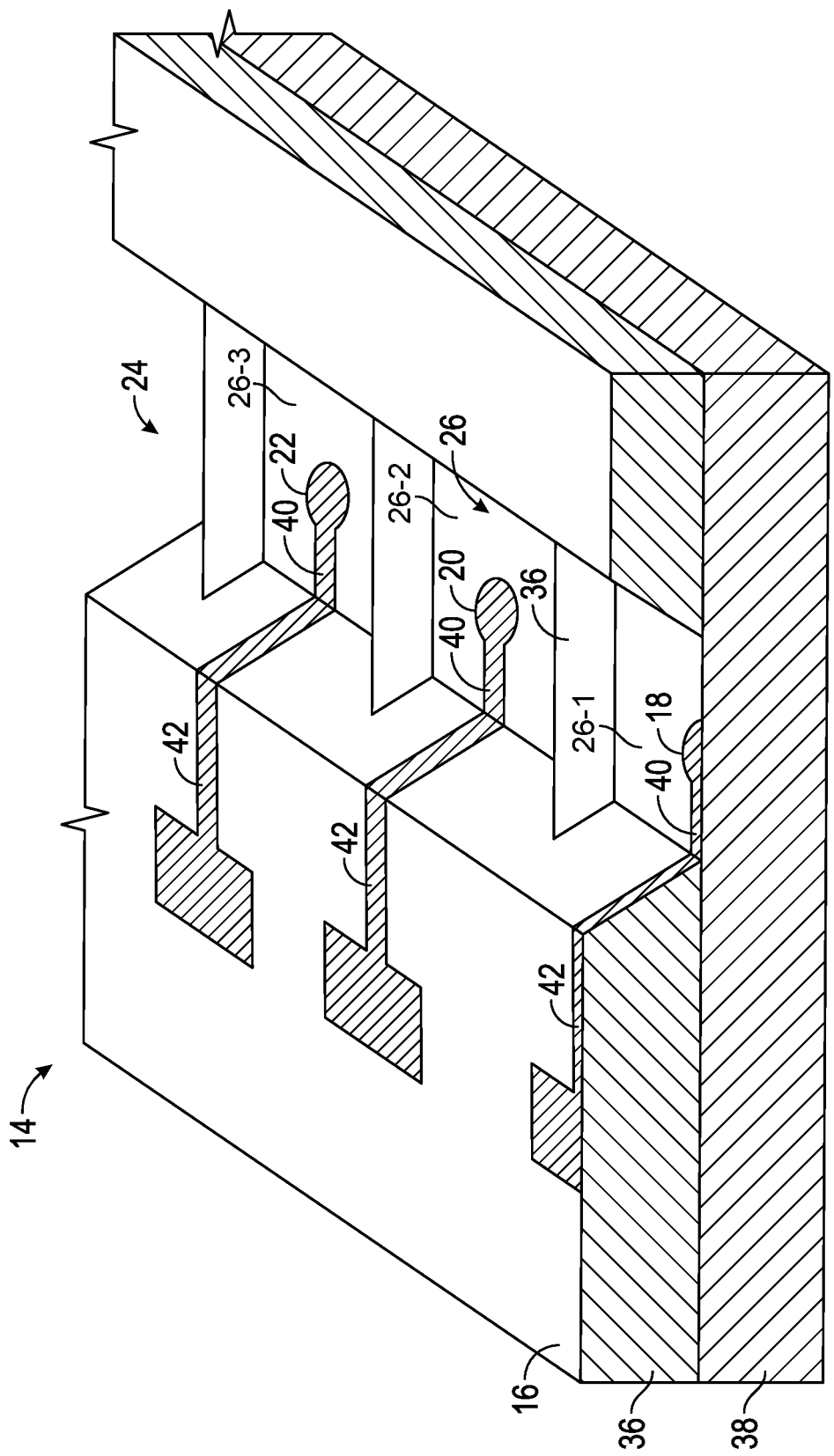
FIG. 2 illustrates a partial cross sectional view of the exemplary embodiment of a plurality of potentiometric sensors taken along the lines 2-2 in FIG. 1 showing a calcium ion selective electrode, a magnesium ion selective electrode, and a reference electrode.

Referring to FIG. 1, the fluid analyzer 10 comprises a fluid channel 24, whereby a fluid, such as a sample, a quality control reagent, and/or a calibration reagent can pass through the fluid channel 24 to come into contact with the plurality of potentiometric sensors 14. Referring now to FIGS. 1 and 2, in one embodiment, a sample, a quality control reagent, and/or a calibration reagent may pass through the fluid channel 24 and into one or more wells 26 defined by the housing 16 supporting and/or encompassing the potentiometric sensors 14. In some embodiments, one or more reference electrodes 22 may be positioned in one or more fluid channels 24 and/or one or more wells 26 of the housing 16. In some embodiments, one or more reference electrodes 22 may be positioned in the one or more fluid channels 24, but not disposed in any of the wells 26.

A sample, quality control reagent, and/or calibration reagent may flow through the fluid channel 24 by a driving force provided by a driving device 28. The driving force 28 may include, but is not limited to, capillary force, pressure, gravity, vacuum, electrokinesis, and/or the like. The driving force may be provided by, for example but without limitation, a pump.

In some embodiments, solvent(s) may be used as a solution to deliver the sample to the potentiometric sensors 14 via the fluid channel 24. In some embodiments, the solvent may deliver the sample to the potentiometric sensors 14 via the fluid channel 24, and then the solvent may evaporate. Evaporation of the solvent(s) may cure one or more membranes on the surface of the particular electrodes including, for example, the interfering ion selective electrode 18, the primary ion selective electrode 20, and the one or more reference electrodes 22. The sample can be introduced into the fluid channel 24 via a sample injection port 30. The sample injection port 30 may be in communication with a valve 32 that can be manually or machine opened and/or closed to allow and/or prevent the sample from entering the fluid channel 24. The sample can be manually or injected or injected by a machine into the sample injection port 30.

In some embodiments, the fluid channel 24 may be a hollow channel. Alternatively, a portion and/or the entire fluid channel 24 may be filled with a carrier material. For example, in some embodiments, a portion and/or the entire fluid channel 24 may be filled with filter paper, gel, and/or beads. The fluid channel 24 also may comprise a waste output 34, whereby the sample, calibration reagent, and/or quality control reagent exits the fluid channel 24 after contacting at least one, and preferably all, of the plurality of potentiometric sensors 14.

Referring to FIG. 2, in one embodiment, the fluid channel 24 may deliver the sample to one or more wells 26, three of which are labeled as 26-1, 26-2, and 26-3. Each of the wells 26 may intersect with one of the potentiometric sensors 14, including, for example but without limitation, the interfering ion selective electrode 18, the primary ion selective electrode 20, and the one or more reference electrodes 22. In some embodiments, one of the wells 26 may intersect with two, or three, or more electrodes from the group consisting of the interfering ion selective electrode 18, the primary ion selective electrode 20, and the one or more reference electrodes 22. For example, although not depicted in FIG. 2, two or more potentiometric sensors 14 may be positioned within a single well 26. In some embodiments, one or more of the potentiometric sensors 14 may be solely positioned within the fluid channel 24 and not within the well(s) 26.

In some embodiments, each of the wells 26 may be shaped to house at least one type of electrode including, for example, the interfering ion selective electrode 18, the primary ion selective electrode 20, and the one or more reference electrodes 22. In some embodiments, size and/or shape of each of the wells 26 may be formed based on effects of an electroactive area for each conductive electrode, effects of deposition volume for membrane dispensing, and/or containment of membrane components. For example, size and shape of the wells 26 may be determined such that the migration and/or interference of membrane components discussed herein may be minimized.

In some embodiments, the wells 26 may be a hollow channel. Alternatively, a portion and/or the entire well(s) 26 may be filled with a carrier material. For example, in some embodiments, a portion and/or the entire well(s) 26 may be filled with filter paper, gel, and/or beads. In some embodiments, the same material(s) may be used to fill the well(s) 26 and the fluid channel 24. Alternatively, different material(s) may be used to fill the well(s) 26 and the fluid channel 24.

In some embodiments, the housing 16 may include a laminate layer 36. One or more wells 26 may be formed within the laminate layer 36. The laminate layer 36 may be formed of a dielectric material, including, but not limited to, plastic, ceramic, glass, and/or the like. In some embodiments, the laminate layer 36 may be patterned to form a part of the well(s) 26 intersecting the one or more reference electrodes 22 and may be formed through removal of portions of the laminate layer 36. Alternatively, the well(s) 26 may be formed via a mold having each well 26 shaped therein, or deposition of a material onto a substrate around each well 26.

The housing 16 may also include a substrate 38 which may be physically configured to receive electrodes including, for example, the interfering ion selective electrode 18, the primary ion selective electrodes 20, and the one or more reference electrodes 22 upon a surface of the substrate 38. In some embodiments, the substrate 38 may be formed of a rigid material. Alternatively, the substrate 38, or a portion of the substrate 38, may be formed of a flexible material.

The substrate 38 may be formed of materials including, but not limited to, plastic, ceramic, glass, and/or any material capable of containing electrodes. For example, in some embodiments, the substrate 38 may be formed of polyethylene terephthalate (PET).

The electrodes for the plurality of potentiometric sensors 14 including, for example, the interfering ion selective electrode 18, the primary ion selective electrode 20, and the one or more reference electrodes 22 may include a conductive layer(s) 40. The conductive layer(s) 40 may be formed of any suitable conductive material including, but not limited to, carbon, silver, silver chloride, gold, platinum, palladium, and/or the like. The conductive layer(s) 40 may be sputtered, electroplated, screen printed, inkjet printed, and/or any other technique capable of applying conductive material to the housing 16 associated with fabrication of the potentiometric sensors 14.

In some embodiments, the conductive layer(s) 40 may be formed by laser ablation of a gold sputtered metal film on a backing with the laminate layer 36 defining the one or more wells 26 wherein, for example, the interfering ion selective electrode 18, the primary ion selective electrode 20, and the one or more reference electrodes 22, along with any additional electrodes, will be placed. Alternatively, in some embodiments, the conductive layer(s) 40 may be formed of localized positioning of a carbon within the housing 16. As illustrated in FIGS. 1 and 2, the electrodes including, for example but without limitation, the interfering ion selective electrode 18, the primary ion selective electrode 20, and the one or more reference electrodes 22 may also include leads 42 for connection to a meter 44.

Generally, the meter 44 receives signals generated by the interfering ion selective electrode 18, primary ion selective electrode 20, and the one or more reference electrodes 22 in contact with a fluid comprising one or more analytes, such as a sample, a quality control reagent, and/or a calibration reagent and transforms the signals into information indicative of the electric potentials of the one or more analytes in the fluid. The analytes can be, for example but without limitation, ions commonly found in biological samples like, e.g., magnesium ions, calcium ion, potassium ions, and/or sodium ions, partial oxygen pressure (pO2), glucose, and/or lactate. In one embodiment, when the interfering ion selective electrode 18 is a calcium ion selective electrode and the primary ion selective electrode 20 is a magnesium ion selective electrode, the meter 44 will be an EMF meter capable of reading the electric potential between one of the reference electrodes 22 and the interfering ion (e.g., calcium ion) selective electrode 18 and the electric potential between one of the reference electrodes 22 and the primary ion (e.g., magnesium ion) selective electrode 20.

In another embodiment, the meter 44 can be any appropriate reader as would be known to a person of ordinary skill in the art when the analyte to be measured by one or more of the potentiometric sensors 14 is not magnesium ions and/or calcium ions. For example, the meter 44 for a sodium ion selective electrode and one of the reference electrodes 22 can be at least one of a voltmeter and/or a pH meter.

In some embodiments, the fluid analyzer 10 may include an amphoteric sensor (not shown in FIG. 1) in communication with the fluid channel 24 in order to obtain measurements for additional analytes including, for example but without limitation, partial oxygen pressure (pO2), glucose, and/or lactate. The amphoteric sensor may include leads 42 for connection to the meter 44.

In some embodiments, the fluid analyzer 10 may further comprise one or more calibration reagent injection ports 46-1, 46-2, and 46-3 which may be in fluidic communication with the fluid channel 24. The calibration reagent injection ports 46 may also be in communication with valves 48-1, 48-2, and 48-3 that can be manually or machine opened and/or closed to allow and/or prevent one or more calibration reagents from entering the fluid channel 24. The valves 48-1, 48-2, and 48-3 can be automated valves that can open or close upon receipt of a suitable control signal.

In some embodiments, the one or more calibration reagent injection ports 46-1, 46-2, and 46-3 can be in fluidic communication with a calibration cartridge 12 comprising one or more calibration reagents.

In one embodiment, the calibration cartridge 12 comprises at least three reservoirs 50-1, 50-2, and 50-3 comprising at least three calibration reagents having different known amounts of ions including, for example but without limitation, magnesium ions ($Mg^{2+}$), calcium ions ($Ca^{2+}$), and, optionally, sodium ions ($Na^+$) and/or potassium ions ($K^+$). The three reservoirs 50-1, 50-2, 50-3 may be, in one embodiment, three individual bags contained within the calibration cartridge 12 having at least three ports that correspond to the one or more calibration reagent injection ports 46-1, 46-2, and 46-3.

In one non-limiting embodiment, the calibration cartridge 12 comprises three calibration reagents, wherein each calibration reagent is contained in one of the three reservoirs 50-1, 50-2, and 50-3. In one embodiment, each of the at least three calibration reagents comprises (a) magnesium ions at a concentration in a range of from about 0.1 mM to about 1.5 mM and (b) calcium ions at concentration in a range of from about 0.2 mM to about 2.0 mM. In one embodiment, the magnesium ions and calcium ions for each of the at least three calibration reagents are at concentrations which differ from each other within the ranges of from about 0.1 to about 1.5 mM for the magnesium ions and about 0.2 to about 2.0 mM for the calcium ions.

Referring again to FIG. 1, the meter 44, driving device 28, and valves 32, 48-1, 48-2, and 48-3, may be in communication with a control system 52 via signal paths 54. The signal paths 54, as shown in FIG. 1, may be, for example but without limitation, one or more cables which convey the data produced by the meter 44 to the controls system 52 and/or information, signals, commands from the controls system 52 to the valves 32, 48-1, 48-2, and 48-3, in electronic form and/or via a network as described in detail herein. The control system 52 may be a system or systems that are able to embody and/or execute the logic of the processes described herein. Logic embodied in the form of software instructions and/or firmware may be executed on any appropriate hardware. For example, logic embodied in the form of software instructions and/or firmware may be executed on dedicated system or systems, on a personal computer system, on a distributed processing computer system, and/or the like. In some embodiments, logic may be implemented in a stand-alone environment operating on a single computer system and/or logic may be implemented in a networked environment such as a distributed system using multiple computers and/or processors.

In one embodiment, a cartridge comprising one or more quality control reagents (not pictured) can be in fluidic communication with one or more quality control reagent injection ports (not pictured) that are in fluidic communication with the fluid channel 24. In one embodiment, the quality control injection port(s) (not pictured) can be in fluidic communication with one or more quality control reagent valves (not pictured), whereby the quality control reagent valve(s) (not pictured) can be manually or machine opened and/or closed to allow and/or prevent the quality control reagent(s) from entering the fluid channel 24. The quality control reagent valves (not pictured) can be automated valves that can open or close upon receipt of a suitable control signal.

Figure 3:
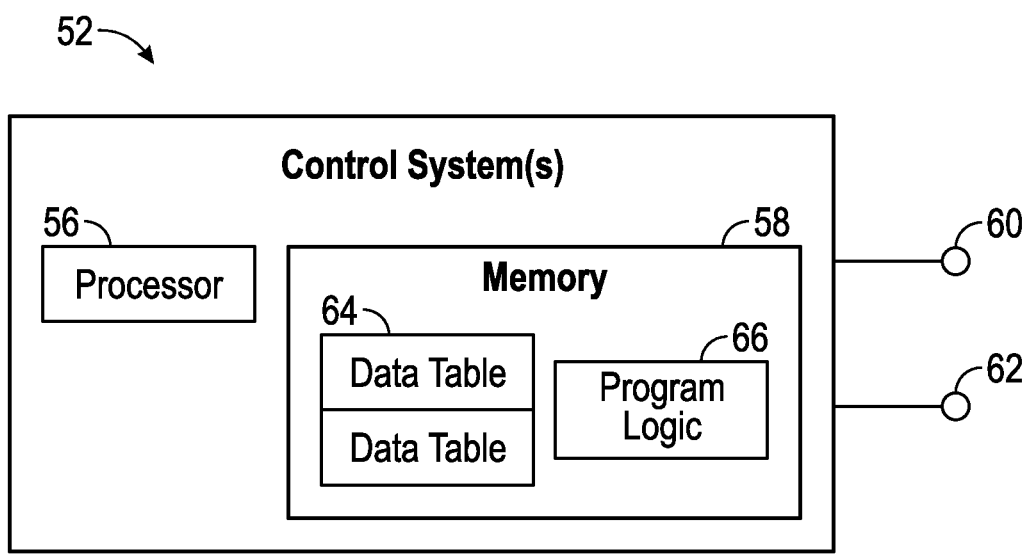
FIG. 3 illustrates a block diagram a control system used in the fluid analyzer depicted in FIG. 1.

Shown in FIG. 3 is a block diagram of the control system 52 which may include one or more processors 56 (hereinafter "processor 56") working together, or independently, to execute processor executable code, one or more memories 58 (hereinafter "memory 58") capable of storing processor executable code, one or more input devices 60 (hereinafter "input device 60"), and one or more output devices 62 (hereinafter "output device 62").

Each element of the controls system 52 may be partially or completely network-based or cloud based, and may or may not be located in a single physical location. In some embodiments, the processor 56 may communicate with the meter 44, driving device 28, and/or one or more valves 32, 48-1, 48-2, and 48-3 via a network. As used herein, the terms "network-based", "cloud-based", and any variations thereof, are intended to include the provision of configurable computational resources on demand via interfacing with a computer and/or computer network, with software and/or data at least partially located on the computer and/or computer network. The network may permit bi-directional communication of information and/or data between the processor 56. The network may interface with the processor 56 and the meter 44, driving device 28, and/or one or more valves 32, 48-1, 48-2, and 48-3 in a variety of ways. For example, but without limitation, the network may interface by optical and/or electronic interfaces, and/or may use a plurality of network topographies and/or protocols including, but not limited to, Ethernet, TCP/IP, circuit switched paths, combinations thereof, and/or the like. For example, in some embodiments, the network may be implemented as the World Wide Web (or Internet), a local area network (LAN), a wide area network (WAN), a metropolitan network, a wireless network, a cellular network, a GSM-network, a CDMA network, a 3G network, a 4G network, a satellite network, a radio network, an optical network, a cable network, a public switch telephone network, an Ethernet network, combinations thereof, and/or the like. Additionally, the network may use a variety of protocols to permit bi-directional interface and/or communication of data and/or information between the processor 56 and the meter 44, driving device 28, and/or one or more valves 32, 48-1, 48-2, and 48-3.

In some embodiments, the network may be the Internet and/or other network. For example, if the network is the Internet, a primary user interface of the control system 52 may be delivered through a series of web pages (e.g., pH and/or $Mg^{2+}$ concentration determination webpages). It should be noted that the primary user interface of the control system 52 may also be another type of interface including, but not limited to, a Windows-based application.

The processor 56 may be implemented as a single processor or multiple processors working together, or independently, to execute the logic as described herein. It is to be understood, that in certain embodiments when using more than one processor 56, the processors 56 may be located remotely from one another, located in the same location, or comprising a unitary multi-core processor. The processor 56 may be capable of reading and/or executing processor executable code and/or capable of creating, manipulating, retrieving, altering and/or storing data structure into the memory 58.

Exemplary embodiments of the processor 56 may include, but are not limited to, a digital signal processor (DSP), a central processing unit (CPU), a field programmable gate array (FPGA), a microprocessor, a multi-core processor, combinations thereof, and/or the like, for example. In some embodiments, additional processors 56 may include, but are not limited to, implementation as a personal computer, a cellular telephone, a smart phone, network-capable television set, a television set-top box, a tablet, an e-book reader, a laptop computer, a desktop computer, a network-capable handheld device, a video game console, a server, a digital video recorder, a DVD-player, a Blu-Ray player, and/or combinations thereof, for example.

The processor 56 may be capable of communicating with the memory 58 via a path (e.g., data bus). The processor 56 may also be capable of communicating with the input device 60 and/or the output device 62.

The processor 56 may be capable of interfacing and/or communicating with the meter 44, driving device 28, and/or one or more valves 32, 48-1, 48-2, and 48-3. For example, the processor 56 may be capable of communicating by exchanging signals (e.g., analog, digital, optical, and/or the like) using a network protocol.

The memory 58 may be capable of storing processor executable code. Additionally, the memory 58 may be implemented as a conventional non-transient memory, such as, for example, random access memory (RAM), a CD-ROM, a hard drive, a solid state drive, a flash drive, a memory card, a DVD-ROM, a floppy disk, an optical drive, combinations thereof, and/or the like.

In some embodiments, the memory 58 may be located in the same physical location as the processor 56, and/or the memory 58 may be located remotely from the processor 56. For example, the memory 58 may be located remotely from the processor 56 and communicate with other processors via the network. Additionally, when more than one memory 58 is used, a first memory may be located in the same physical location as the processor 56, and additional memories 58 may be located in a remote physical location from the processor 56. Additionally, the memory 58 may be implemented as a "cloud memory" (i.e., one or more memories 58 may be partially or completely based on or accessed using the network).

The input device 60 may be capable of receiving information input from a user and/or processor(s) 56, and may be capable of transmitting such information to the processor 56, network, and/or meter 44, driving device 28, and/or one or more valves 32, 48-1, 48-2, 48-3. The input device 60 may include, but is not limited to, implementation as a keyboard, touchscreen, mouse, trackball, microphone, fingerprint reader, infrared port, slide-out keyboard, flip-out keyboard, cell phone, PDA, video game controller, remote control, fax machine, network interface, combinations thereof, and the like, for example.

The output device 62 may be capable of outputting information in a form perceivable by a user and/or processors(s) 56. For example, the output device 62 may include, but is not limited to, implementation as a computer monitor, a screen, a touchscreen, a speaker, a website, a television set, a smart phone, a PDA, a cell phone, a fax machine, a printer, a laptop computer, combinations thereof, and/or the like, for example. It is to be understood that in some exemplary embodiments, the input device 60 and the output device 62 may be implemented as a single device, such as, for example, a touchscreen or a tablet. It is to be further understood that as used herein the term user is not limited to a human being, and may comprise a computer, a server, a website, a processor, a network interface, a human, a user terminal, a virtual computer, combinations thereof, and/or the like, for example.

Figure 4:
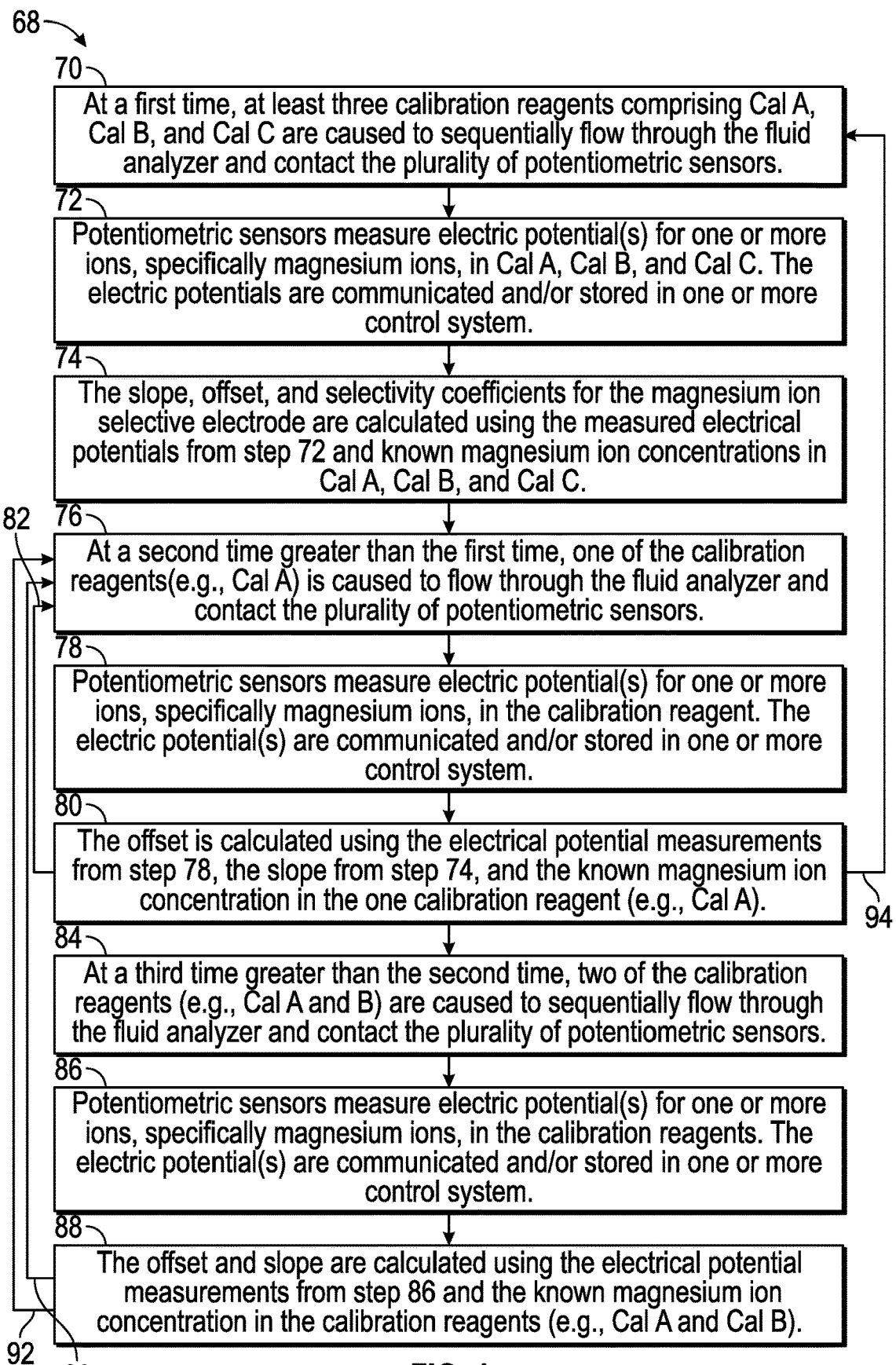
FIG. 4 illustrates a flow chart of an exemplary in-line method for calibrating a potentiometric magnesium ion sensor.

The memory 58 may store processor executable code and/or information comprising one or more databases and/or data tables 64 and program logic 66 (also referred to herein as "calibration logic"). In some embodiments, the processor executable code may be stored as a data structure, such as a database and/or a data table 64, for example. In some embodiments, outputs of the meter 44, driving device 28, and/or one or more valves 32, 48-1, 48-2, 48-3 may be stored in one or more databases and/or data tables 64 within the memory 58. FIG. 4 illustrates a flow chart 68 of an exemplary method for calibrating the processor 56 to properly interpret signals from the primary ion selective electrode 20 in the fluid analyzer 10 at instants of time within a time interval including but not limited to >28 days. Other methods may be envisioned for the order in which the calibration steps are carried out as illustrated in the one or more examples included herewith. The calibration can be conducted on a timed basis. In particular, the flow chart 68 illustrates an exemplary method for calibrating a magnesium ion selective electrode in the fluid analyzer 10 on a timed basis wherein the magnesium ion selective electrode is the primary ion selective electrode 20 and the interfering ion selective electrode 18 is a calcium ion selective electrode, as depicted in FIG. 1, such that the processor 56 of the fluid analyzer 10 is capable of accurately and precisely measuring the level of magnesium ions in, for example, a blood sample over the uselife of a solid state magnesium ion sensor (i.e., at least approximately 28 days).

In a step 70, at a first time period, at least three calibration reagents comprising a first calibration reagent ("Cal A"), a second calibration reagent ("Cal B"), and a third calibration reagent ("Cal C") may be sequentially provided into the fluid analyzer 10 via the one or more calibration reagent injection ports 46-1, 46-2, and 46-3. In one embodiment, the first time period begins at time=0, which may be the start of the wetup period of the solid state magnesium ion sensor.

In one embodiment, the first calibration reagent ("Cal A") is in fluidic communication with calibration reagent injection port 46-1, the second calibration reagent ("Cal B") is in fluidic communication with calibration reagent injection port 46-2, and the third calibration reagent ("Cal C") is in fluidic communication with calibration reagent injection port 46-3. As described above, the three calibration reagents can be contained within a calibration cartridge 12 comprising three reservoirs 50-1, 50-2, 50-3 having at least three ports that correspond to the calibration reagent injection ports 46-1, 46-2, and 46-3

The at least three calibration reagents, Cal A, Cal B, and Cal C, may also be controllably introduced into the fluid analyzer 10 by valves 48-1, 48-2, and 48-3, which may be manually opened/closed or automatically opened/closed by the processor 56. In one embodiment, the valves 48-1, 48-2, and 48-3 are automatically opened and closed via a transitory or non-transitory signal indicative of a command transmitted along one or more signal paths 54 from the control system 52 to the appropriate valves 48-1, 48-2, and 48-3. The processor(s) 56 of the control system 52 may have memory 58 in which processor executable code may be stored relating to a timed basis for sending the transitory or non-transitory signal indicative of commands from the control system 52 to automatically open and/or close the valves 48-1, 48-2, and 48-3.

All three calibration reagent injection ports 46-1, 46-2, and 46-3 may be in fluidic communication with the fluid channel 24 by way of the valves 48-1, 48-2, and 48-3.

The at least three calibration reagents comprising Cal A, Cal B, and Cal C introduced into the fluid analyzer 10 in sequential order may flow through the fluid channel 24 by the driving force provided by the driving device 28. The driving force 28 may include, but is not limited to, capillary force, pressure, gravity, vacuum, electrokinesis, and/or the like. The driving force 28 may be provided by, for example but without limitation, a pump. The at least three calibration reagents comprising Cal A, Cal B, and Cal C may flow through the fluid channel 24 such that each calibration reagent comes into contact with the plurality of potentiometric sensors 14 comprising the interfering ion selective electrode 18, the primary ion selective electrode 20, and the one or more reference electrodes 22. In one embodiment, the interfering ion selective electrode 18 is a calcium ion selective electrode and the primary ion selective electrode 20 is a magnesium ion selective electrode.

In one embodiment, the driving device 28 may be automatically engaged (i.e., turned on) prior to or at the same time as the one or more valves 48-1, 48-2, and 48-3 are opened via a transitory or non-transitory signal indicative of a command transmitted along one or more signal paths 54 from the control system 52 to the driving device 28. The processor(s) 56 of the control system 52 may have memory 58 in which processor executable code may be stored relating to a timed basis for sending the transitory or non-transitory signal indicative of a command from the control system 52 to automatically engage the driving device 28 prior to or at the same time as the valves 48-1, 48-2, and 48-3 are opened.

In a step 72, the plurality of potentiometric sensors 14 sequentially contacted by the at least three calibration reagents comprising Cal A, Cal B, and Cal C generate electric potentials between the ion selective electrodes 18 and 20 therein and the one or more reference electrodes 22 for each of the at least three calibration reagents, which are capable of being detected and measured by the meter 44. The electric potential(s) measured by the meter 44 can be transmitted via a transitory or non-transitory signal from the meter 44 to the control system 52 via one or more signal paths 54.

In one embodiment, the plurality of potentiometric sensors 14 comprises a calcium ion selective electrode, a magnesium ion selective electrode, and one or more reference electrodes 22 sequentially contacted by the at least three calibration reagents comprising Cal A, Cal B, and Cal C. For each calibration reagent, the electric potential difference between (i) the calcium ion selective electrode and the one or more reference electrodes 22 and (ii) the electric potential difference between the magnesium ion selective electrode and the one or more reference electrode(s) 22 can be individually detected and measured by the meter 44, in particular by one or more EMF meters. The electric potential(s) measured by the EMF meter can be transmitted via a transitory or non-transitory signal(s) therefrom to the control system 52 via one or more signal paths 54.

The electric potential(s) measured by the meter 44 and transmitted to the control system 52 as a transitory or non-transitory signal(s) via one or more signal paths 54 can be stored in the memory 58 within the control system 52.

Three Point Calibration ("Full Calibration")

In a step 74, using the program logic 66 of the control system 52, the processor 56 (also referred to herein as "calibration logic" for the first three point calibration and "re-calibration logic" for any subsequent three point calibrations) may calibrate the way the processor 56 interprets data from the magnesium ion selective electrode relative to data from the one or more reference electrodes 22 (also referred to herein as "calibrating the magnesium ion selective electrode") by using the electric potentials measured by the meter 44 for the at least three calibration reagents comprising Cal A, Cal B, and Cal C in light of the known magnesium ion concentrations and calcium ion concentrations of the calibration reagents which may be stored in, for example, the memory 58 within the control system 52. The known magnesium ion concentrations and calcium ion concentrations for the at least three calibration reagents may be input into the control system 52 via one or more input devices 60 and stored in the memory 58.

In one embodiment, using the program logic 66 of the control system 52, the processor 56 calibrates the magnesium ion selective electrode by calculating the slope, offset, and selectivity coefficient of the magnesium ion selective electrode using (i) the electric potentials measured by the meter 44 for the at least three calibration reagents comprising Cal A, Cal B, and Cal C, (ii) the known magnesium ion concentrations and calcium ion concentrations in the calibration reagents, and (iii) the Nernstian equation and Nicolsky-Eisenman equation, all of which can be stored in, for example, memory 58 within the control system 52. As used herein, the term "calibration information" may refer to one or more of the slope, offset, and/or selectivity coefficient of the Nernstian equation or Nicolsky-Eisenman equation.

Presented below is one non-limiting example of the program logic 66 that calibrates the magnesium ion selective electrode using (i) the electric potentials measured by the meter 44 for the at least three calibration reagents comprising Cal A, Cal B, and Cal C, (ii) the known magnesium ion concentrations and calcium ion concentrations in the calibration reagents, and (iii) the Nernstian equation and Nicolsky-Eisenman equation, all of which can be stored in, for example, the memory 58 within the control system 52:

First, the slope of the Nernstian Equation may be calculated as follows:

$$\text{Slope 1} = (E_{CalA} - E_{CalC}) / [\log(Mg_{CalA}^{2+}) - \log(Mg_{CalC}^{2+})] \quad \text{(III)}$$

"$E_{CalA}$" is the electric potential of the magnesium ions in Cal A, as measured by the meter 44 that is in communication with the magnesium ion selective electrode when Cal A is in contact therewith; "$E_{CalC}$" is the electric potential of the magnesium ions in Cal C, as measured by the meter 44 that is in communication with the magnesium ion selective electrode when Cal C is in contact therewith; "$Mg_{CalA}^{2+}$" is the known concentration of magnesium ions in Cal A; and "$Mg_{CalA}^{2+}$" is the known concentration of magnesium ions in Cal C. The slope (i.e., "Slope 1") may be stored in the memory 58 and/or transmitted to the output device 62 via one or more signal paths 54.

Second, using the calculated slope ("Slope 1"), the offset of the Nernstian Equation may be calculated as follows:

$$\text{Offset 1} = E_{calA} - (\text{Slope 1}) * \log(Mg_{CalA}^{2+}) \quad \text{(IV)}$$

"$E_{CalA}$" is the electric potential of the magnesium ions in Cal A, as measured by the meter 44 that are in communication with the magnesium ion selective electrode when Cal A is in contact therewith; "$Mg_{CalA}^{2+}$" is the known concentration of magnesium ions in Cal A; and "Slope 1" is the slope of the Nernstian Equation calculated in the first step. The offset (i.e., "Offset 1") may be stored in the memory 58 and/or transmitted to the output device 62 via one or more signal paths 54.

Third, using the calculated slope ("Slope 1") and offset ("Offset 1") of the Nernstian Equation from the first two steps, the selectivity coefficient ("Sel 1") of the Nicolsky-Eisenman equation may be calculated via "Iteration #1" as follows:

$$\text{Sel 1} = \{[10^{\wedge}((E_{CalB} - \text{Offset 1})/\text{Slope 1}) - 10^{\wedge}((E_{CalC} - \text{Offset 1})/\text{Slope 1})] - (Mg_{CalB}^{2+} - Mg_{CalC}^{2+})\} / (Ca_{CalB}^{2+} - Ca_{CalC}^{2+}) \quad \text{(V)}$$

"$E_{CalB}$" is the electric potential of the magnesium ions in Cal B, as measured by the meter 44 that is in communication with the magnesium ion selective electrode when Cal B is in contact therewith; "Offset 1" and "Slope 1" are the offset and slope values of the Nernstian Equation calculated in the first two steps; "$E_{CalC}$" is the electric potential of the magnesium ions in Cal C, as measured by the meter 44 that are in communication with the magnesium ion selective electrode when Cal C is in contact therewith; "$Mg_{CalB}^{2+}$" is the known concentration of magnesium ions in Cal B; "$Mg_{CalC}^{2+}$" is the known concentration of magnesium ions in Cal C; "$Ca_{CalB}^{2+}$" is the known concentration of calcium ions in Cal B; and "$Ca_{CalC}^{2+}$" is the known concentration of calcium ions in Cal C. The selectivity coefficient (i.e., "Sel 1") may be stored in the memory 58 and/or transmitted to the output device 62 via one or more signal paths 54.

Next, the slope, offset, and selectivity values may be iteratively calculated "n" amount of times in a manner exemplified below in "Iteration #2" until an $n^{th}$ selectivity coefficient ("Sel N") is obtained. An example of the iterative calculation carried out by the processor 56 running the program logic 66 of the control system 52 is illustrated below using the previously determined Slope 1, Offset 1, and Sel 1 as well as (i) the electric potentials measured by the meter 44 for the at least three calibration reagents comprising Cal A, Cal B, and Cal C, (ii) the known magnesium ion concentrations and calcium ion concentrations in the calibration reagents, and (iii) the Nernstian equation and Nicolsky-Eisenman equation, all of which can be stored in, for example, the memory 58 within the control system 52:

Iteration #2:

The second slope value ("Slope 2") may be calculated using the Nicolsky Eisenman Equation and the selectivity coefficient calculated from the first set of calculations, i.e., "Sel 1". In particular, Slope 2 is calculated as follows:

$$\text{Slope } 2 = (E_{CalA} - E_{CalC})/[\log(Mg_{CalB}^{2+} + (Sel\ 1)^*(Ca_{CalA}^{2+})) - \log(Mg_{CalC}^{2+} + (Sel\ 1)^*(Ca_{CalC}^{2+}))] \quad (VI)$$

"$E_{CalA}$" is the electric potential of the magnesium ions in Cal A, as measured by the meter 44 that is in communication with the magnesium ion selective electrode when Cal A is in contact therewith; "$E_{CalC}$" is the electric potential of the magnesium ions in Cal C, as measured by the meter 44 that is in communication with the magnesium ion selective electrode when Cal C is in contact therewith; "$Mg_{CalB}^{2+}$" is the known concentration of magnesium ions in Cal B; "Sel 1" is the selectivity coefficient calculated above; "$Ca_{CalA}^{2+}$" is the known concentration of calcium ions in Cal A; "$Mg_{CalC}^{2+}$" is the known concentration of magnesium ions in Cal C; and "$Ca_{CalC}^{2+}$" is the known concentration of calcium ions in Cal C. The slope (i.e., "Slope 2") may be stored in the memory 58 and/or transmitted to the output device 62 via one or more signal paths 54.

The second offset value ("Offset 2") may be calculated using the Nicolsky Eisenman Equation and "Slope 2" and "Sel1". In particular, Offset 2 may be calculated as follows:

$$\text{Offset } 2 = E_{CalA} - (\text{Slope } 2)^*(\log(Mg_{CalB}^{2+} + Sel1^*Ca_{CalA}^{2+})) \quad (VII)$$

"$E_{CalA}$" is the electric potential of the magnesium ions in Cal A, as measured by the meter 44 that is in communication with the magnesium ion selective electrode when Cal A is in contact therewith; "$Mg_{CalB}^{2+}$" is the known concentration of magnesium ions in Cal B; "$Ca_{CalA}^{2+}$" is the known concentration of calcium ions in Cal A; "Sel 1" is the selectivity coefficient calculated above; and "Slope 2" is the slope calculated above. The offset (i.e., "Offset 2") may be stored in the memory 58 and/or transmitted to the output device 62 via one or more signal paths 54.

The second selectivity coefficient ("Sel 2") may be calculated using the Nicolsky Eisenman Equation using the above-calculated Slope 2 and Offset 2. In particular, Sel 2 is calculated as follows:

$$Sel\ 2 = \{[10^{\wedge}((E_{CalB} - \text{Offset } 2)/\text{Slope } 2) - 10^{\wedge}((E_{CalC} - \text{Offset } 2)/\text{Slope } 2)] - (Mg_{CalB}^{2+} - Mg_{CalC}^{2+})\}/(Ca_{CalB}^{2+} - Ca_{CalC}^{2+}) \quad (VIII)$$

"$E_{CalB}$" is the electric potential of the magnesium ions in Cal B, as measured by the meter 44 that is in communication with the magnesium ion selective electrode when Cal B is in contact therewith; "Offset 2" and "Slope 2" are the above-calculated offset and slope values; "$E_{CalC}$" is the electric potential of the magnesium ions in Cal C, as measured by the meter 44 that is in communication with the magnesium ion selective electrode when Cal C is in contact therewith; "$Mg_{CalB}^{2+}$" is the known concentration of magnesium ions in Cal B; "$Mg_{CalC}^{2+}$" is the known concentration of magnesium ions in Cal C; "$Ca_{CalB}^{2+}$" is the known concentration of calcium ions in Cal B; and "$Ca_{CalC}^{2+}$" is the known concentration of calcium ions in Cal C. The selectivity coefficient (i.e., "Sel 2") may be stored on the memory 58 and/or transmitted to the output device 62 via one or more signal paths 54.

As previously noted, the iterative calculations of the slope, offset, and selectivity values can be repeated in a similar manner as exemplified in "Iteration #2" (replacing "Sel 1" with "Sel 2" to find "Slope 3", for example, and so on) an "n" amount of times until a $n^{th}$ selectivity coefficient ("Sel N") is calculated. For each iteration: (1) the slope (e.g., Slope N) may be calculated using the selectivity from the previous iteration (e.g., Slope N–1), (2) the offset (e.g., Offset N) may be calculated using the corresponding slope (e.g., Slope N), and (3) the selectivity (e.g., Sel N) may be calculated using the corresponding values of Offset N and Slope N. Such a calculation is presented below as "Iteration #N":

$$\text{Slope } N = \frac{E_{CalA} - E_{CalC}}{\log(Mg_{CalB}^{2+} + (Sel\ N - 1)*(Ca_{CalA}^{2+})) - \log(Mg_{CalC}^{2+} + (Sel\ N)*(Ca_{CalC}^{2+}))} \quad (IX)$$

$$\text{Offset } N = E_{CalA} - (\text{Slope } N - 1)*\log(Mg_{CalA}^{2+} + Sel(N-1)*Mg_{CalA}^{2+}) \quad (X)$$

$$Sel\ N = \{[10^{\wedge}((E_{CalB} - \text{Offset } N)/\text{Slope } N) - 10^{\wedge}((E_{CalC} - \text{Offset } N)/\text{Slope } N)] - (Mg_{CalB}^{2+} - Mg_{CalC}^{2+})\}/(Ca_{CalB}^{2+} - Ca_{CalC}^{2+}) \quad (XI)$$

The iteration may be carried out until the selectivity coefficient becomes stable. In one embodiment, the selectivity coefficient may be determined as stable when it varies less than ±1%, or less than about 0.75%, or less than about 0.5%, or less than about 0.25% from the calculation immediately prior. In one embodiment, the number of iterations, "n", is greater than 20, or greater than 21, or greater than 22, or greater than 23, or greater than 24, or greater than 25, or greater than 26, or greater than 27, or greater than 28, or greater than, 29, or greater than 30. The selectivity coefficient (i.e., "Sel N") may be stored in the memory 58 and/or transmitted to the output device 62 via one or more signal paths 54.

Steps 70, 72, 74 may also be referred to herein as the "Three Point Calibration", "Full Calibration method", or simply "Full Calibration."

In a step 76, at a second time period greater than the first time period, one of the at least three calibration reagents comprising Cal A, Cal B, and Cal C (e.g., Cal A) is provided into the fluid analyzer 10 in a similar manner as previously described for the at least three calibration reagents—except, of course, with respect to only one of the calibration reagents. That is, in a step 76, at a second time period greater than the first time period, Cal A, for example, is provided into the fluid analyzer 10 via one or more calibration reagent injection ports 46-1, 46-2, and 46-3. In one embodiment, Cal A is in fluidic communication with calibration reagent injection port 46-1.

The memory 58 of the processor(s) 56 of the control system 52 may store processor executable code relating to a timed basis for sending a transitory or non-transitory signal(s) indicative of a command from the control system 52 to automatically engage the driving device 28 and/or the one or more valves 48-1, 48-2, and/or 48-3 in fluidic communication with Cal A such that Cal A is automatically introduced into the fluid analyzer 10 and contacted with the plurality of potentiometric sensors 14 at the prescribed second time period.

The second time period can be less than or equal to about 5 minutes, or less than or equal to about 10 minutes, or less than or equal to about 15 minutes, or less than or equal to about 20 minutes, or less than or equal to about 25 minutes, or less than or equal to about 30 minutes after the first time period. In one embodiment, the second time period is less than or equal to about 30 minutes after the first time period. In another embodiment, the second time period is about 30 minutes after the first time period.

In a step 78, the plurality of potentiometric sensors 14 contacted by only one of the at least three calibration reagents, e.g., Cal A, generate electric potentials between the ion selective electrodes 18 and 20 therein and the one or more reference electrodes 22. These electric potentials are capable of being detected and measured by the meter 44. The electric potential(s) measured by the meter 44 can be transmitted via a transitory or non-transitory signal from the meter 44 to the control system 52 via one or more signal paths 54.

As above, the plurality of potentiometric sensors 14 may comprise a calcium ion selective electrode, a magnesium ion selective electrode, and one or more reference electrodes 22 contacted by the calibration reagent, e.g., Cal A. The electric potential difference between (i) the calcium ion selective electrode and the one or more reference electrodes 22 and (ii) the electric potential difference between the magnesium ion selective electrode and the one or more reference electrode(s) can be individually detected and measured by the meter 44, in particular by one or more EMF meters. The electric potential(s) measured by the EMF meters can be transmitted via a transitory or non-transitory signal(s) to the control system 52 via one or more signal paths 54.

The electric potential(s) measured by the meter 44 and transmitted to the control system 52 as a transitory or non-transitory signal(s) via one or more signal paths 54 can be can be stored in the memory 58 within the control system 52.

One Point Calibration

In a step 80, using the program logic 66 (also referred to herein as "re-calibration logic") of the control system 52, the processor 56 may calibrate the way the processor 56 interprets data from the magnesium ion selective electrode by using the electric potentials measured by the meter 44 for the calibration reagent used in step 76 in light of the known magnesium ion concentrations and calcium ion concentrations of the calibration reagent used in step 76, all of which may be stored in, for example, the memory 58 within the control system 52. The known magnesium ion concentrations and calcium ion concentrations for the calibration reagent used in step 76 may be input into the control system 52 via one or more input devices 60 and stored in the memory 58.

In one embodiment, in step 80, the processor 56 calibrates the magnesium ion selective electrode by calculating the offset of the magnesium ion selective electrode using the program logic 66 of the control system 52 in combination with (i) the electric potentials measured by the meter 44 for the calibration reagent used in step 76, (ii) the known magnesium ion concentrations and calcium ion concentrations in the calibration reagent used in step 76, (iii) the slope calculated in step 74 (i.e., "Slope N"), and (iv) the Nicolsky-Eisenman equation, all of which can be stored in, for example, the memory 58 within the control system 52. The offset calculated in step 80 is also referred to herein as "re-calibration information" since it uses information from the initial three point calibration to calibrate the magnesium ion sensor.

Presented below is one non-limiting example of the program logic 66 that is capable of calibrating a magnesium ion selective electrode using (i) the electric potentials measured by the meter 44 for the calibration reagent used in step 76, (ii) the known magnesium ion concentrations and calcium ion concentrations in the calibration reagent used in step 76, (iii) the slope calculated in step 74 (i.e., "Slope N"), and (iv) the Nicolsky-Eisenman equation, all of which can be stored in, for example, the memory 58 within the control system 52:

$$\text{Offset} = E_{CalA} - (\text{Slope } N) * \log(Mg_{CalA}^{2+}) \quad \text{(XII)}$$

"$E_{CalA}$" is the electric potential of the magnesium ions in Cal A, as measured by the meter 44 that are in communication with the magnesium ion selective electrode when Cal A is in contact therewith; "$Mg_{CalA}^{2+}$" is the known concentration of magnesium ions in Cal A; and "Slope N" is the slope determined after "n" iterations in step 74. The offset value may be stored on the memory 58 and/or transmitted to the output device 62 via one or more signal paths 54.

Steps 76, 78, and 80 may be referred to herein as the "One Point Calibration Method" or simply the "One Point Calibration".

In a step 82, steps 76, 78, and 80 are repeated x number of times. Each time, an Offset is calculated as previously described and stored in the memory 58 and/or transmitted to the output device 62 via one or more signal paths 54. The number of repetitions, x, in step 82 can be 2 or 3 or 4 or 5 or 6 or 7 or 8 or 9 or 10. In one embodiment, the number of repetitions is 2, such that the series of steps 76, 78, and 80 calculating the offset are carried out a total of 3 times before moving to step 84. Each repetition may be carried out within 5 minutes, or within 10 minutes, or within 15 minutes, or within 20 minutes, or within 25 minutes, or within 30 minutes after the completion of the series of steps 76, 78, and 80. In one embodiment, each repetition is carried out within 30 minutes after the completion of the prior series of steps 76, 78, 80. In one embodiment, each repetition is carried out about 30 minutes after the completion of the prior series of steps 76, 78, and 80.

The memory 58 of the processor(s) 56 of the control system 52 may store processor executable code relating to a timed basis for sending a transitory or non-transitory signal(s) indicative of a command from the control system 52 to automatically engage the driving device 28 and/or the valves 48-1, 48-2, and/or 48-3 in fluidic communication with one of the at least three calibration reagents, e.g., Cal A, such that the calibration reagent is automatically introduced into the fluid analyzer 10 and contacted with the plurality of potentiometric sensors 14 for the prescribed repetition number and at the desired time period.

In a step 84, at a third time period greater than both the first time period and the second time period, two of the at least three calibration reagents comprising Cal A, Cal B, and Cal C (e.g., Cal A and Cal B) are provided into the fluid analyzer 10 in a similar manner as previously described for the at least three calibration reagents—except, of course, with respect to only two of the calibration reagents. That is, in a step 84, at a third time period, which is greater than the first time period and second time period, Cal A and Cal B, for example, are sequentially provided into the fluid analyzer 10 via one or more calibration reagent injection ports 46-1, 46-2, and 46-3. In one embodiment, Cal A is in fluidic communication with calibration reagent injection port 46-1 and Cal B is in fluidic communication with calibration reagent injection port 46-2.

The memory 58 of the processor(s) 56 of the control system 52 may store processor executable code relating to a timed basis for sending a transitory or non-transitory signal(s) indicative of a command from the control system 52 to automatically engage the driving device 28 and/or the valves 48-1, 48-2, and/or 48-3 in fluidic communication with Cal A and/or Cal B such that Cal A and Cal B are sequentially introduced into the fluid analyzer 10 and sequentially contacted with the plurality of potentiometric sensors 14 at the prescribed third time period, which is greater than the first time period and the second time period.

The third time period can be less than or equal to about 5 minutes, or less than or equal to about 10 minutes, or less than or equal to about 15 minutes, or less than or equal to about 20 minutes, or less than or equal to about 25 minutes, or less than or equal to about 30 minutes, or less than or equal to about 1 hour, or less than or equal to about 2 hours, or less than or equal to about 3 hours, or less than or equal to about 4 hours, or less than or equal to about 5 hours, or less than or equal to about 6 hours, or less than or equal to about 7 hours, or less than or equal to about 8 hours after the first time period. In one embodiment, the third time period is less than or equal to about two hours after the first time period. In another embodiment, the third time period is about two hours after the first time period.

In a step 86, the plurality of potentiometric sensors 14 sequentially contacted by two of the at least three calibration reagents, e.g., Cal A and Cal B, generate electric potentials between the ion selective electrodes 18 and 20 therein and the one or more reference electrodes 22. These electric potentials are capable of being detected and measured by the meter 44. The electric potential(s) measured by the meter 44 can be transmitted via a transitory or non-transitory signal from the meter 44 to the control system 52 via one or more signal paths 54.

As above, the plurality of potentiometric sensors 14 comprises a calcium ion selective electrode, a magnesium ion selective electrode, and one or more reference electrodes 22 contacted by the two calibration reagents, e.g., Cal A and Cal B. The electric potential difference between (i) the calcium ion selective electrode and the one or more reference electrodes 22 and (ii) the electric potential difference between the magnesium ion selective electrode and the one or more reference electrode(s) can be individually detected and measured by the meter 44, in particular by one or more EMF meters. The electric potential(s) measured by the EMF meters can be transmitted via a transitory or non-transitory signal(s) therefrom to the control system 52 via one or more signal paths 54.

The electric potential(s) measured by the meter 44 and transmitted to the control system 52 as a transitory or non-transitory signal(s) via one or more signal paths 54 can be can be stored in the memory 58 within control system 52.

In a step 88, using the program logic 66 of the control system 52, the processor 56 may calibrate the way the processor 56 interprets data from the magnesium ion selective electrode by using the electric potentials measured by the meter 44 for the two calibration reagents, e.g., Cal A and Cal B, in step 86 in light of the known magnesium ion concentrations and calcium ion concentrations of the two calibration reagents used in step 84 which may be stored in, for example, the memory 58 within the control system 52. The known magnesium ion concentrations and calcium ion concentrations for the calibration reagent(s) used in steps 84 and 86 may be input into the control system 52 via one or more input devices 60.

Two Point Calibration

In one embodiment, in step 88, the processor 56 calibrates the magnesium ion selective electrode by calculating the slope and offset of the magnesium ion selective electrode using the program logic 66 of the one or more control systems 52 in combination with (i) the electric potentials measured by the meter 44 for the calibration reagents in step 86, (ii) the known magnesium ion concentrations and calcium ion concentrations in the calibration reagents used in steps 84 and 86, (iii) the selectivity coefficient calculated in step 74 (i.e., "Sel N"), and (iv) the Nicolsky-Eisenman equation, all of which can be stored in, for example, the memory 58 within the control system 52. The offset and slope calculated in step 86 is also referred to herein as "re-calibration information" since it uses information derived from the initial three point calibration to calibrate the magnesium ion sensor.

Presented below is one non-limiting example of the program logic 66 (also referred to herein as "re-calibration logic") that calibrates the magnesium ion selective electrode by finding an additional slope ("Slope 2PT") and an Offset ("Offset 2PT") using (i) the electric potentials measured by the meter 44 for the two calibration reagents in step 86 (e.g., Cal A and Cal B), (ii) the known magnesium ion concentrations and calcium ion concentrations in the two calibration reagents used in steps 84 and 86 (e.g., Cal A and Cal B), (iii) the selectivity coefficient calculated in step 74 (i.e., "Sel N"), and (iv) the Nicolsky-Eisenman equation, all of which can be stored in, for example, the memory 58 within the control system 52.

First the two point slope (or "Slope 2PT") may be calculated as follows:

$$\text{Slope } 2PT = \frac{E_{CalA} - E_{CalB}}{\log(Mg^{2+}_{CalA} + (Sel\ N)*(Ca^{2+}_{CalA})) - \log(Mg^{2+}_{CalB} + (Sel\ N)*(Ca^{2+}_{CalB}))} \quad \text{(XIII)}$$

"$E_{CalA}$" is the electric potential of the magnesium ions in Cal A, as measured by the meter 44 that is in communication with the magnesium ion selective electrode when Cal A is in contact therewith; "$E_{cam}$" is the electric potential of the magnesium ions in Cal B, as measured by the meter 44 that is in communication with the magnesium ion selective electrode when Cal B is in contact therewith; "$Mg_{CalA}^{2+}$" is the known concentration of magnesium ions in Cal A; "Sel N" is the selectivity coefficient calculated in step 74; "$Ca_{CalA}^{2+}$" is the known concentration of calcium ions in Cal A; "$Mg_{CalB}^{2+}$" is the known concentration of magnesium ions in Cal B; and "$Ca_{CalB}^{2+}$" is the known concentration of calcium ions in Cal B. The slope (i.e., "Slope 2PT") may be stored on the memory 58 and/or transmitted to the output device 62 via one or more signal paths 54.

Secondly, using the calculated Slope 2PT, the offset can be calculated as follows:

$$\text{Offset } 2PT = E_{CalA} - (\text{Slope } 2PT)*\log(Mg_{CalA}^{2+}) \quad \text{(XIV)}$$

"$E_{CalA}$" is the electric potential of the magnesium ions in Cal A, as measured by the meter 44 that are in communication with the magnesium ion selective electrode when Cal A is in contact therewith; "$Mg_{CalA}^{2+}$" is the known concentration of magnesium ions in Cal A; and "Slope 2PT" is the above-described slope. The offset value may be stored in the memory 58 and/or transmitted to the output device 62 via one or more signal paths 54.

Steps 84, 86, and 88 may be referred to herein as the "Two Point Calibration Method" or simply the "Two Point Calibration".

In a step 90, the method returns to step 76, whereby steps 76, 78, and 80 are again carried out to calculate the offset using the "Slope 2PT" value from step 88 instead of Slope N. Step 82 is also again carried out, whereby steps 76, 78, and 80 are repeated x number of times. Each time, an Offset is calculated as previously described and stored on the memory 58 and/or transmitted to the output device 62 via one or more signal paths 54. As previously described, the number of repetitions, x, in step 82 can be 2 or 3 or 4 or 5 or 6 or 7 or 8 or 9 or 10. In one embodiment, the number of repetitions is 2, such that the series of steps 76, 78, and 80. Each repetition may be carried out within 5 minutes, or within 10 minutes, or within 15 minutes, or within 20 minutes, or within 25 minutes, or within 30 minutes after the completion of the series of steps 76, 78, and 80. In one embodiment, each repetition is carried out within 30 minutes after the completion of the prior series of steps 76, 78, 80. In one embodiment, each repetition is carried out about 30 minutes after the completion of the prior series of steps 76, 78, and 80.

Additionally, after step 82 has been carried out x number of times, steps 84, 86, and 88 are again carried out to calculate a slope ("Slope 2PT") and an offset ("Offset 2PT") based on the selectivity coefficient calculated in step 74 ("Sel N"). The slope and offset values may be stored on the memory 58 and/or transmitted to the output device 62 via one or more signal paths 54.

Step 90 can be repeated "y" number of times. The number of repetitions of step 90, y, can be 2 or 3 or 4 or 5 or 6 or 7 or 8 or 9 or 10. In one embodiment, the number of repetitions, y, is 2, such that the entire series of steps 76, 78, 80, 82, 84, 86, and 88 is carried out a total of 3 times before moving to step 92. Each repetition may be carried out within 5 minutes, or within 10 minutes, or within 15 minutes, or within 20 minutes, or within 25 minutes, or within 30 minutes, after the completion of steps 76, 80, 82, 84, 86, and 88 until the number of repetitions, y, is reached. In one embodiment, the step 90 occurs about every 5 minutes, or about every 10 minutes, or about every 15 minutes, or about every 20 minutes, or about every 30 minutes, or about every hour, or about every 2 hours, or about every 3 hours, or about every 4 hours, or about every 5 hours, or about every 6 hours, or about every 7 hours, or about every 8 hours after step 70 until the number of repetitions, y, is reached. In one embodiment, step 90 occurs about every 2 hours after step 70 until the number of repetitions, y, is reached.

The memory 58 of the processor(s) 56 of the control system 52 may store processor executable code relating to a timed basis for sending a transitory or non-transitory signal(s) indicative of a command from the control system 52 to automatically engage the driving device 28 and/or the valves 48-1, 48-2, and/or 48-3 in fluidic communication with two of the at least calibration reagents, e.g., Cal A and Cal B, such that the calibration reagents are automatically introduced into the fluid analyzer 10 and contacted with a plurality of potentiometric sensors 14 for the prescribed repetition numbers for steps 82 and 90 and at the desired times.

In a step 92, the method again returns to step 76, whereby steps 76, 78, and 80 are carried out to calculate the offset using the "Slope 2PT" value from the latest repetition of step 88. Step 82 is also again carried out, whereby steps 76, 78, and 80 are repeated x number of times. Each time, an Offset is calculated as previously described and stored on the memory 58 and/or transmitted to the output device 62 via one or more signal paths 54. The number of repetitions, x, in step 82 can be 2 or 3 or 4 or 5 or 6 or 7 or 8 or 9 or 10. In one embodiment, the number of repetitions is 2, such that the series of steps 76, 78, and 80 calculating the offset are carried out a total of 3 times before again moving to step 94. Each repetition may be carried out within 5 minutes, or within 10 minutes, or within 15 minutes, or within 20 minutes, or within 25 minutes, or within 30 minutes after the completion of the series of steps 76, 78, and 80. In one embodiment, each repetition is carried out within 30 minutes after the completion of the prior series of steps 76, 78, 80. In one embodiment, each repetition is carried out about 30 minutes after the completion of the prior series of steps 76, 78, and 80. The offset values may be stored on the memory 58 and/or transmitted to the output device 62 via one or more signal paths 54.

At a step 94, after steps 76, 78, and 80 are carried out x times, the method returns to step 70 and steps 70, 72, 74, 76, 80, 82, 84, 86, 88, 90, and 92 are again carried out as previously described. In another embodiment, step 94 can be repeated about every 5 minutes, or about every 10 minutes, or about every 15 minutes, or about every 20 minutes, or about every 30 minutes, or about every hour, or about every 2 hours, or about every 3 hours, or about every 4 hours, or about every 5 hours, or about every 6 hours, or about every 7 hours, or about every 8 hours for approximately 28 days or until the end of the uselife of a solid state magnesium ion sensor. In one embodiment, step 94 is repeated every 8 hours during the uselife of a solid state magnesium ion sensor. In one embodiment, step 94 is repeated every 8 hours for approximately 28 days or until the end of the uselife of a solid state magnesium ion sensor.

In one embodiment, after step 94 returns the method to step 70, the "Slope 2PT" calculated in the most recent repetition of step 88 can be used for establishing the iteration end point criteria for the calculation of slope, offset, and selectivity coefficient in step 74. In one embodiment, the iteration in step 74, as previously described herein, is complete when the slope for the $n^{th}$ iteration becomes stable. In one embodiment, the iteration in step 74 is complete when the slope for the $n^{th}$ iteration is within 1%, or 0.5%, or 0.1%, or 0.05%, or 0.01% of the "Slope 2PT" determined in the most recent repetition of step 88. In one embodiment, the number of iterations, "n", is greater than 20, or greater than 21, or greater than 22, or greater than 23, or greater than 24, or greater than 25, or greater than 26, or greater than 27, or greater than 28, or greater than, 29, or greater than 30.

In another embodiment, the two point calibration, as described above, can be carried out prior to the one point calibration, as described above. In yet another embodiment, the three point calibration begins at time t=0 and then at least one of the one point calibration, two point calibration, and three point calibration can take place in any order as long as at least one calibration method is carried out every 30 minutes and at least one three point calibration is carried out every 8 hours during the uselife of the solid state magnesium ion sensor. Additionally, other methods may be envisioned for the order in which the calibration steps are carried out as illustrated in the one or more examples included herewith.

EXAMPLES

Examples are provided hereinbelow. However, the presently disclosed and/or claimed inventive concept(s) is to be understood to not be limited in its application to the specific experimentation, results, and procedures disclosed hereinbelow. Rather, the Examples are provided as various embodiments and are meant to be exemplary, not exhaustive.

Example 1

A magnesium ion selective electrode for a fluid analyzer was calibrated using the procedure outlined herein to determine (i) an initial selectivity, i.e., "Selectivity N" after "n" iterations using three calibration reagents, Cal A, Cal B, and Cal C, and (ii) a 2 point calibration slope, i.e., "Slope 2PT, using the "Selectivity N" value after "n" iterations.

Figure 5:
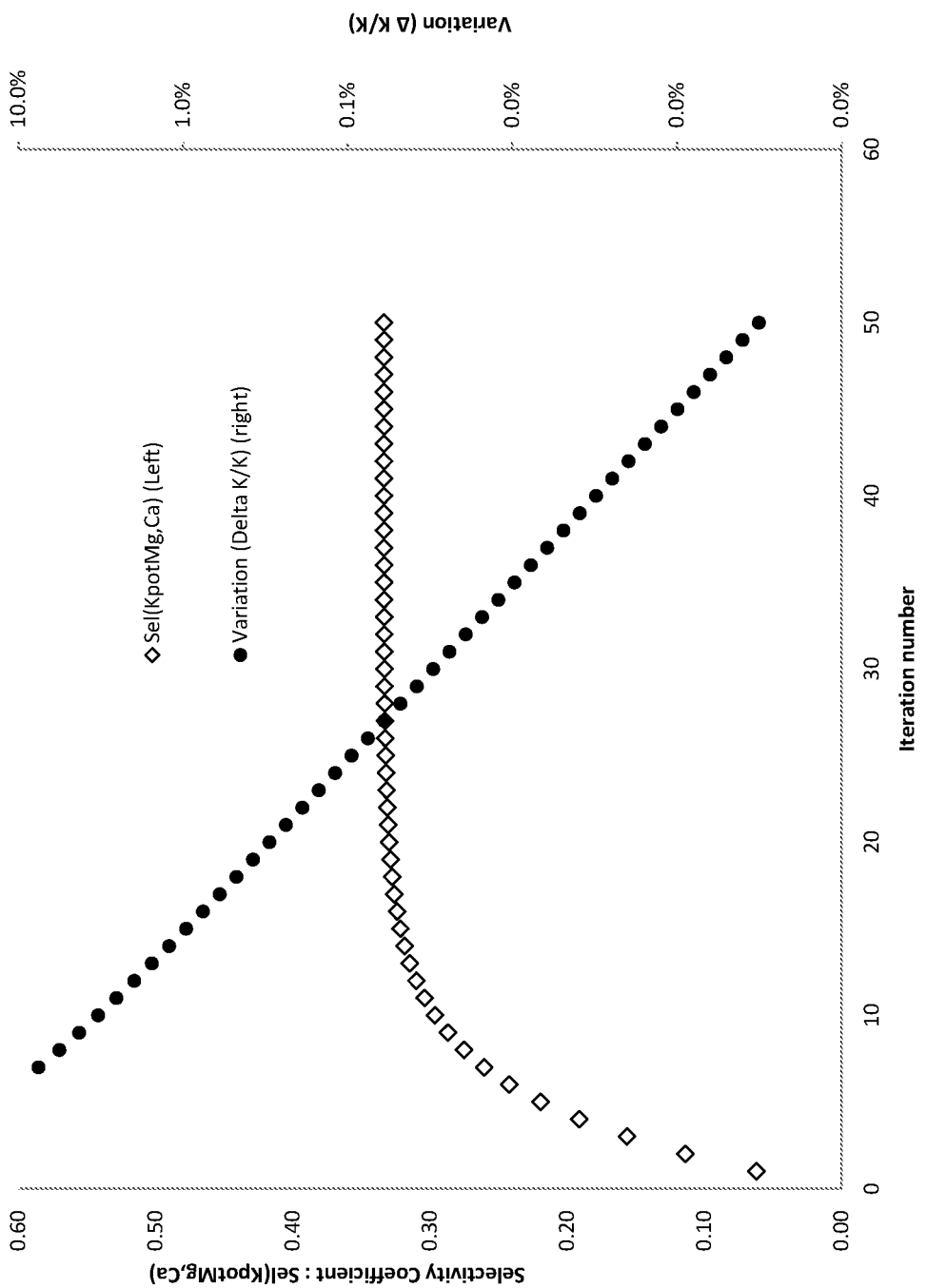
FIG. 5 graphically depicts the selectivity coefficient determined over the course of 50 iterations using three calibration reagents.

At a time t=0, the three calibration reagents were sequentially introduced into the fluid analyzers such that they would individually come into contact with a magnesium ion selective electrode and a reference electrode. This is also referred to as the "Full Calibration". Using equations III-XI and the procedures associated therewith as described herein, a number of iterations were carried out to calculate a stable selectivity coefficient. In this example, n=50 (i.e., 50 iterations were carried out) as illustrated in Table 1 and FIG. 5. As further illustrated in FIG. 5, only about 15 iterations were necessary to arrive at a stable selectivity coefficient of 1%.

TABLE 1

| Iteration number | Sel ($K^{pot}_{Mg,Ca}$) | Variation (Δ K/K) |
|---|---|---|
| 1 | 0.06 | |
| 2 | 0.11 | 83.5% |
| 3 | 0.16 | 37.4% |
| 4 | 0.19 | 22.2% |
| 5 | 0.22 | 14.7% |
| 6 | 0.24 | 10.4% |
| 7 | 0.26 | 7.6% |
| 8 | 0.28 | 5.6% |
| 9 | 0.29 | 4.3% |
| 10 | 0.30 | 3.3% |
| 11 | 0.30 | 2.5% |
| 12 | 0.31 | 2.0% |
| 13 | 0.31 | 1.5% |
| 14 | 0.32 | 1.2% |
| 15 | 0.32 | 1.0% |
| 16 | 0.32 | 0.8% |
| 17 | 0.33 | 0.6% |
| 18 | 0.33 | 0.5% |
| 19 | 0.33 | 0.4% |
| 20 | 0.33 | 0.3% |
| 21 | 0.33 | 0.2% |
| 22 | 0.33 | 0.2% |
| 23 | 0.33 | 0.1% |
| 24 | 0.33 | 0.1% |
| 25 | 0.33 | 0.1% |
| 26 | 0.33 | 0.1% |
| 27 | 0.33 | 0.1% |
| 28 | 0.33 | 0.0% |
| 29 | 0.33 | 0.0% |
| 30 | 0.33 | 0.0% |
| 31 | 0.33 | 0.0% |
| 32 | 0.33 | 0.0% |
| 33 | 0.33 | 0.0% |
| 34 | 0.33 | 0.0% |
| 35 | 0.33 | 0.0% |
| 36 | 0.33 | 0.0% |
| 37 | 0.33 | 0.0% |
| 38 | 0.33 | 0.0% |
| 39 | 0.33 | 0.0% |
| 40 | 0.33 | 0.0% |
| 41 | 0.33 | 0.0% |
| 42 | 0.33 | 0.0% |
| 43 | 0.33 | 0.0% |
| 44 | 0.33 | 0.0% |

TABLE 1-continued

| Iteration number | Sel ($K^{pot}_{Mg,Ca}$) | Variation (Δ K/K) |
|---|---|---|
| 45 | 0.33 | 0.0% |
| 46 | 0.33 | 0.0% |
| 47 | 0.33 | 0.0% |
| 48 | 0.33 | 0.0% |
| 49 | 0.33 | 0.0% |
| 50 | 0.33 | 0.0% |

Figure 6:
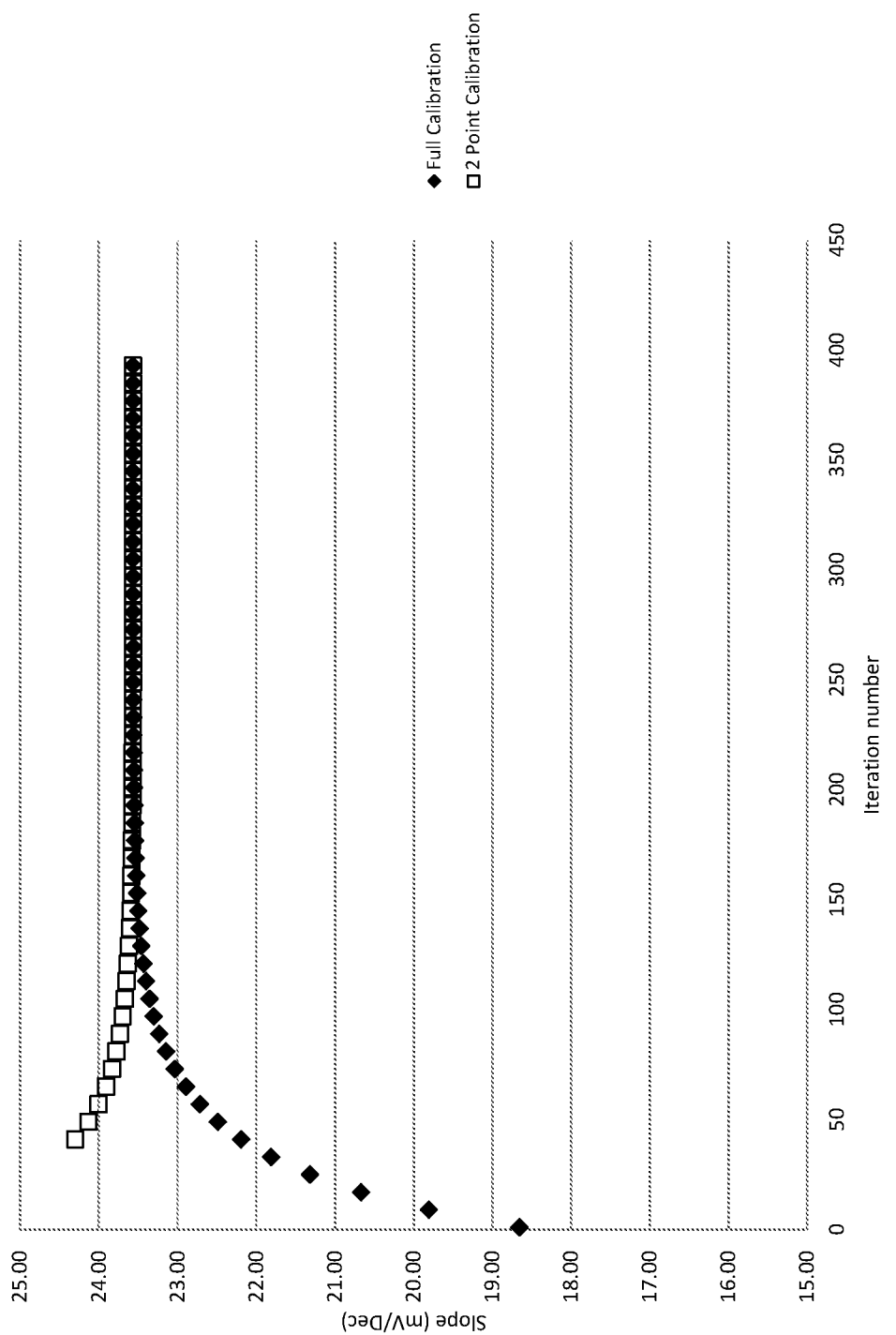
FIG. 6 graphically depicts the convergence of slopes determined by a Full Calibration process (using three calibration reagents) and a Two Point Calibration process (using two calibration reagents and the selectivity coefficient from the Full Calibration process after "n" iterations).

At a time t=2 hours, two of the three calibration reagents were sequentially introduced into the fluid analyzers such that they would come into contact with the magnesium ion selective electrode and reference electrode. This is also referred to as the "2 Point Calibration." Using equation XIII and the procedures associated therewith in addition to the selectivity coefficient calculated from the Full Calibration, a slope, i.e., the "Slope 2PT", can be calculated. As illustrated in FIG. 6, as the number of iterations in the Full Calibration increases, the closer the slope from the Full Calibration gets to the two point slope such that eventually they are identical. This is the basis for being able to use the "Slope 2PT" as end point criteria for the calculation of slope, offset, and selectivity coefficient on later Full Calibrations.

Table 2 presents the composition of the main electrolytes in the three calibration reagents used in Example 1. The calibration reagent most resembling the normal concentration of electrolytes in blood is Cal A. Table 3 presents the known concentrations of magnesium ions and calcium ions in the calibration reagents as well as their respective mV signals detected by their respective ion selective electrodes and measured by one or more EMF sensors.

TABLE 2

| | $Mg^{2+}$ (mM) | $Ca^{2+}$ (mM) | $K^+$ (mM) | $Na^+$ (mM) |
|---|---|---|---|---|
| Cal A | 0.43 | 1.26 | 4 | 115 |
| Cal B | 0.45 | 0.63 | 8 | 160 |
| Cal C | 1.00 | 1.76 | 4 | 75 |

TABLE 3

| | $Mg^{2+}$ (mM) | $Ca^{2+}$ (mM) | $Mg^{2+}$ sensor (mV) | $Ca^{2+}$ sensor (mV) |
|---|---|---|---|---|
| Cal A | 0.43 | 1.26 | −98.8 | 58.0 |
| Cal B | 0.45 | 0.63 | −101.6 | 48.4 |
| Cal C | 1.00 | 1.76 | −93.1 | 61.6 |

Example 2

In order to test the effectiveness of the calibration method, two normal blood samples were tested after the Full Calibration method, the Two Point Calibration method, and the One Point Calibration method. The calibration methods used three calibration reagents having mV signals for magnesium ions and calcium ions as illustrated in Table 3 for the Full Calibration. The iteration number for the Full Calibration was n=50 for this example. Additionally, the solid state magnesium ion sensor was approximately 15 days into its uselife at the time of the Full Calibration, Two Calibration, and One Point calibration and testing.

Three trials of each blood sample were after the Full Calibration, the Two Point Calibration, and the One Point Calibration. The magnesium ion recovery in the blood was calculated by the following equation:

$$C_{Mg^{2+}} = 10^{\frac{mV(sample)-mV(offset)}{slope}} - (Sel\ N) * C_{Ca^{2+}}$$

To ensure that the results were comparable to an FDA approved iMg system, the measurements of a commercial magnesium ion selective electrode analyzer are also included. The commercial magnesium ion selective electrode analyzer is the FDA approved iMg sensor available from NOVA Biomedical (Waltham, Mass.). The results are presented in Table 4.

TABLE 4

| Cal/Sample | Cal Seq. | Time | Mg (mV) | Ca (mV) | Sel. Coeff. | Slope (mV/Dec) | Offset (mV) | Mg ISE Mg$^{2+}$ (mM) | Nova Mg$^{2+}$ (mM) |
|---|---|---|---|---|---|---|---|---|---|
| | | | Iteration Number, n, =50 for Full Calibration | | | | | | |
| Full | Cal A | 0:00 | −99.20 | 52.90 | — | — | — | — | — |
| Full | Cal B | 0:00 | −101.90 | 53.30 | — | — | — | — | — |
| Full | Cal C | 0:00 | −93.50 | 43.70 | 0.31 | 22.70 | −97.6 | — | — |
| 2 PT | Cal A | 6:35 | −98.80 | 54.70 | — | — | — | — | — |
| 2 PT | Cal B | 6:35 | −101.50 | 45.20 | — | 22.70 | −97.2 | — | — |
| 1 PT | Cal A | 7:09 | −98.77 | 54.80 | — | — | −97.2 | — | — |
| Blood Sample - 1 | — | 7:31 | −99.46 | 54.59 | — | — | — | 0.43 | 0.42 |
| Blood Sample - 1 | — | 7:34 | −99.28 | 54.66 | — | — | — | 0.44 | — |
| Blood Sample - 1 | — | 7:37 | −99.34 | 54.73 | — | — | — | 0.43 | — |
| 1 PT Cal | Cal A | 7:42 | −98.90 | 55.10 | — | — | 97.3 | — | — |
| Blood Sample - 2 | — | 7:44 | −98.20 | 55.20 | — | — | — | 0.55 | 0.53 |
| Blood Sample - 2 | — | 7:46 | −98.20 | 55.20 | — | — | — | 0.54 | — |
| Blood Sample - 2 | — | 7:49 | −98.20 | 55.10 | — | — | — | 0.55 | — |

As can be determined from Table 4, the magnesium ion measurements obtained by the presently disclosed and/or claimed calibration method for the blood samples are at least equivalent to the FDA approved iMg system available from NOVA Biomedical. It should be noted that the 2 PT calibration reflected in Table 4 was the third 2PT calibration carried out after the initial Full Calibration. The additional 2PT and 1 PT calibration measurements carried out prior to those noted in Table 4 were not listed in the table in order to clearly highlight the slope and offset calibration measurements taken immediately prior to measuring the Blood Samples.

The calibration approach as described herein was applied to a solid state magnesium ion sensor over 4 weeks—i.e., the approximate uselife of the sensor. Three calibration reagents were used corresponding to Cal A, Cal B, and Cal C illustrated in Tables 2 and 3 above. The calibration schedule is presented below in Table 5.

TABLE 5

| Type of Calibration | Time (Hr) |
|---|---|
| Full Calibration | t = 0 |
| One Point Calibration | t = 0.5 |
| One Point Calibration | t = 1 |
| One Point Calibration | t = 1.5 |
| Two Point Calibration | t = 2 |
| One Point Calibration | t = 2.5 |
| One Point Calibration | t = 3 |

TABLE 5-continued

| Type of Calibration | Time (Hr) |
|---|---|
| One Point Calibration | t = 3.5 |
| Two Point Calibration | t = 4 |
| One Point Calibration | t = 4.5 |
| One Point Calibration | t = 5 |
| One Point Calibration | t = 5.5 |
| Two Point Calibration | t = 6 |
| One Point Calibration | t = 6.5 |
| One Point Calibration | t = 7 |
| One Point Calibration | t = 7.5 |
| Full Calibration | t = 8 |

The schedule is then repeated over the course of the 4 weeks as if the Full Calibration at t=8 hours is the same as the Full Calibration at t=0; however, each Full Calibration from t=8 hours can use the slope from the latest Two Point Calibration as end point criteria for the calculation of slope, offset, and selectivity coefficient.

Figure 7:
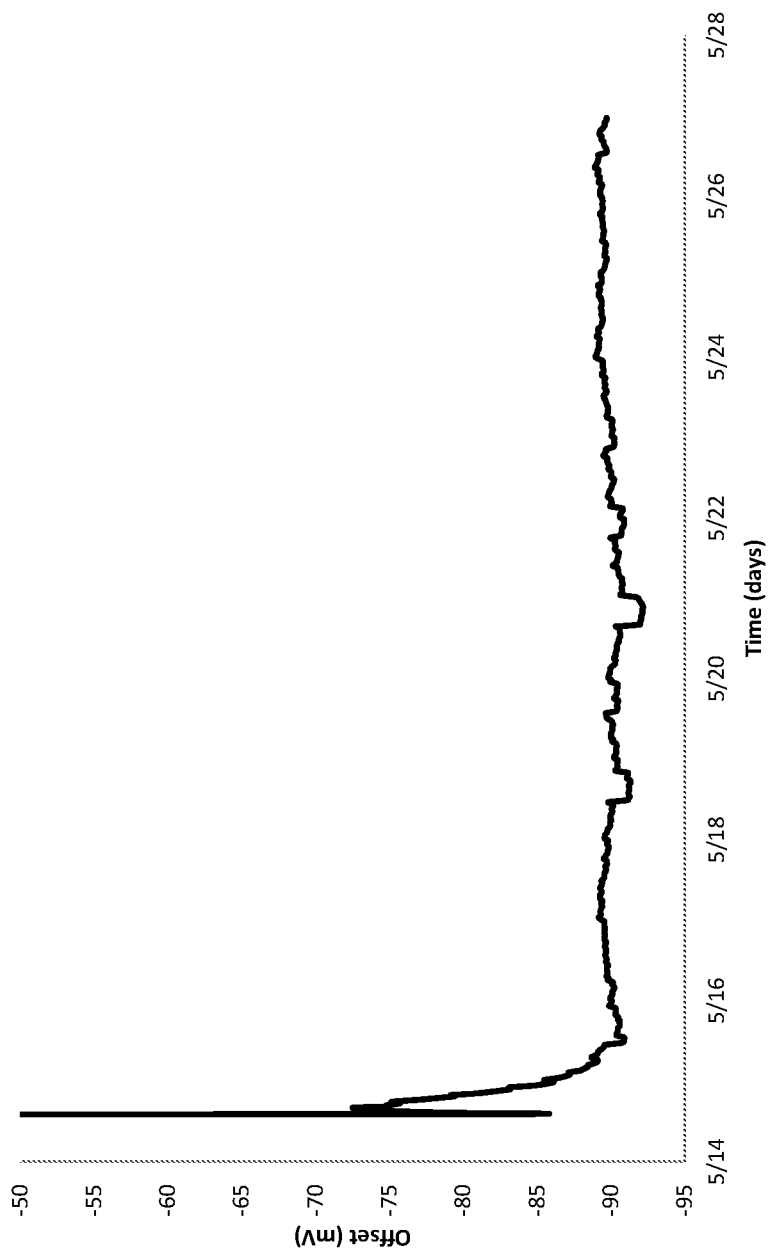
FIG. 7 graphically depicts the offset of a solid state magnesium ion sensor calculated over 4 weeks using the presently disclosed and/or claimed fluid analyzer calibration method.
Figure 8:
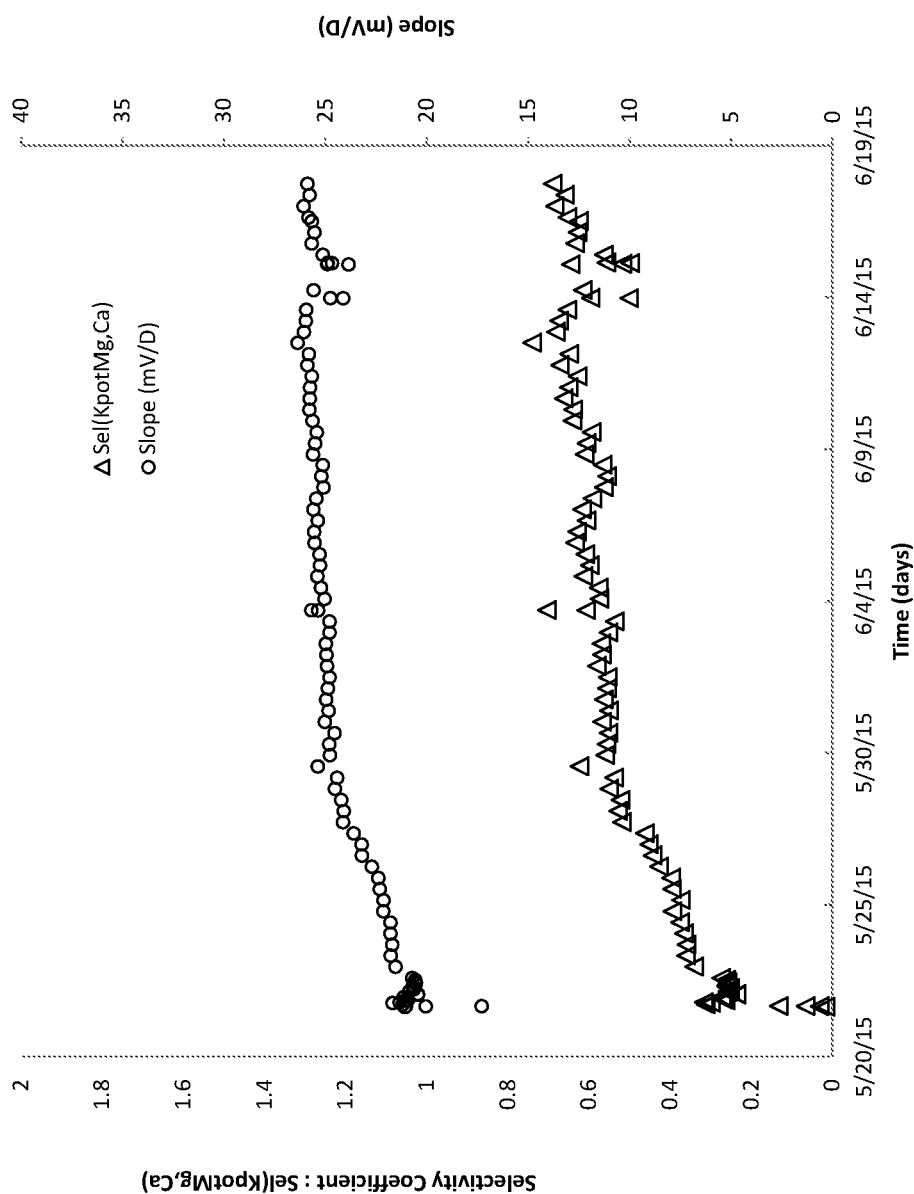
FIG. 8 graphically depicts the selectivity coefficient and slope of a solid state magnesium ion sensor calculated over 4 weeks using the presently disclosed and/or claimed fluid analyzer calibration method.

The calibration parameters of slope, offset, and selectivity coefficient are plotted over the 4 weeks and are illustrated in FIGS. 7 and 8. The variation trend of the magnesium ion selective electrode tracked well with these three parameters. Although FIGS. 7 and 8 initially show unstable values during the initialization period, also referred to as the "wetup period" lasting up to 8 hours, the Mg$^{2+}$ recovery, i.e., the measured concentration of magnesium ions, in the quality control and/or blood samples was stable during this time period due to the calibration method disclosed and/or claimed herein, as exemplified in FIG. 9. This indicates that the presently disclosed and/or claimed calibration method is capable of adequately calibrating an iMg sensor even during the initial wetup period.

Figure 9:
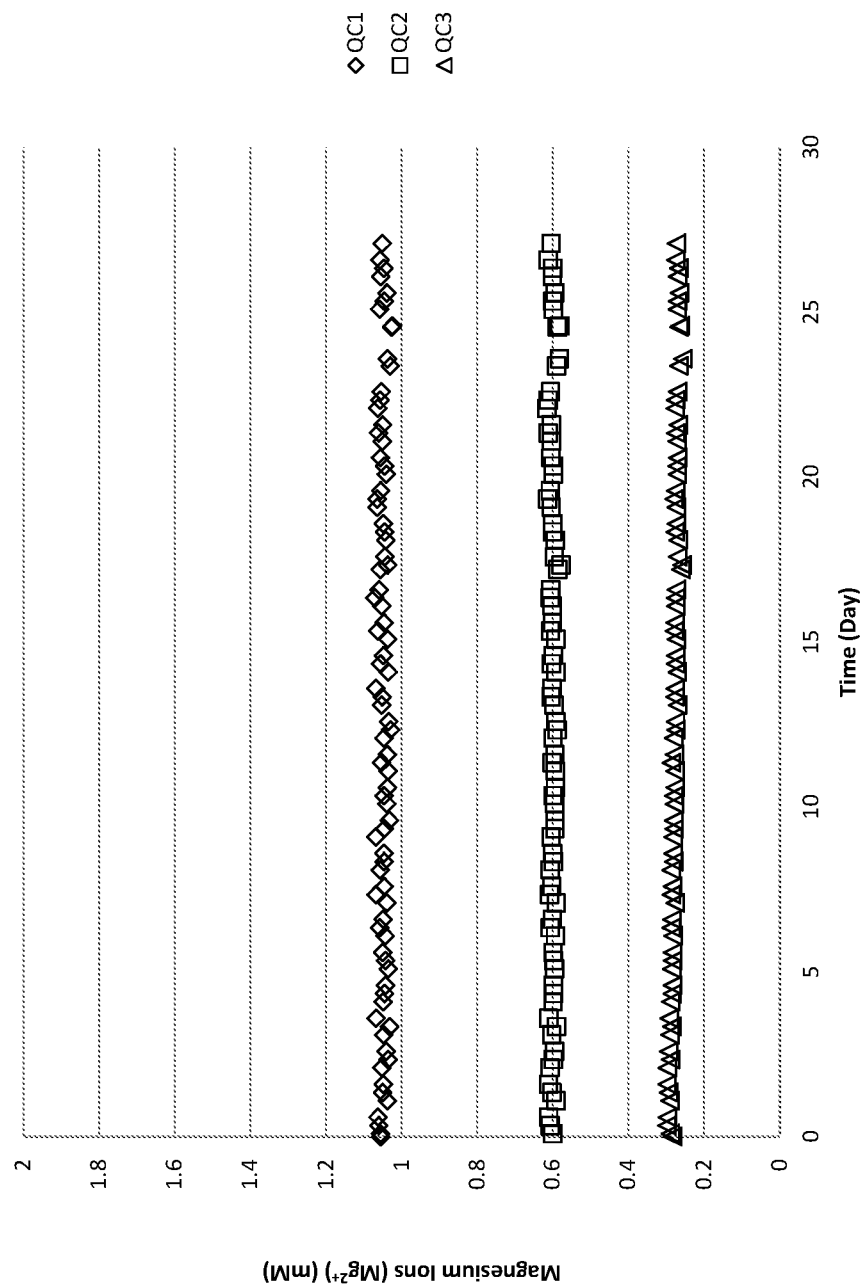
FIG. 9 graphically depicts the measured quantities of magnesium ions of three quality controls having three magnesium ion concentrations over 4 weeks using the presently disclosed and/or claimed fluid analyzer calibration method.
Figure 10:
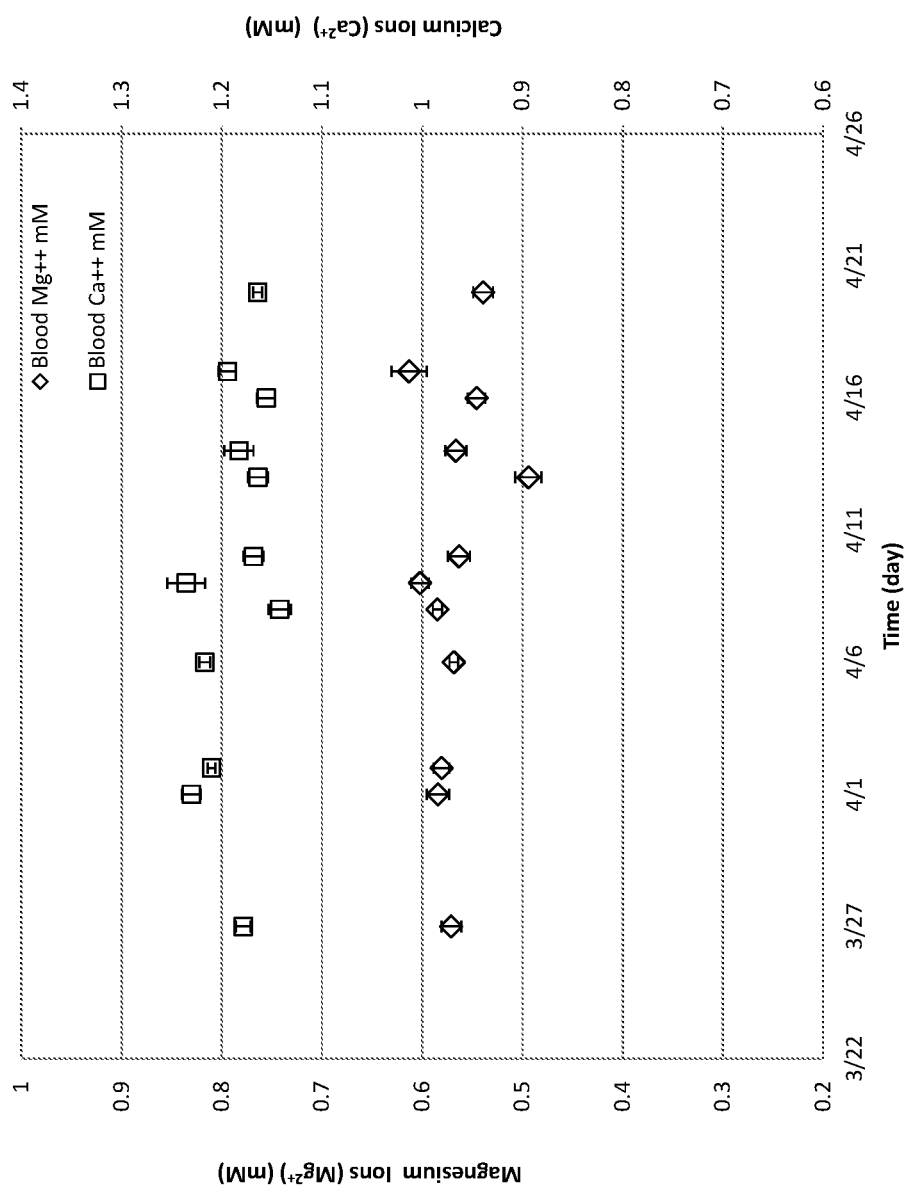
FIG. 10 graphically depicts the measured quantities of magnesium ions and calcium ions of an unaltered blood over 4 weeks using the presently disclosed and/or claimed fluid analyzer calibration method for the magnesium ion selective electrode.

Aqueous control solutions at three magnesium ion levels (1.0 mM, 0.6 mM, and 0.3 mM) were tested throughout the 4 weeks as shown in FIG. 9. Unaltered blood samples were also tested throughout the 4 weeks. FIG. 10 illustrates the magnesium ion recoveries of the unaltered blood samples obtained using the calibration method described and/or claimed herein alongside the calcium ion recoveries of the unaltered blood samples as assayed with a current commercial calcium ion selective electrode (Siemens RAPIDPoint 500 blood gas analyzer's calcium ions sensor). As illustrated in FIG. 10, the high precision magnesium ion recovery using the presently disclosed and/or claimed calibration method is comparable to the precision of the calcium ion recovery assayed with the current commercial calcium ion selective electrode.

Therefore, in accordance with the presently disclosed and/or claimed inventive concept(s), there have been provided a fluid analyzer for measuring magnesium ions and a method of calibrating the magnesium ion selective electrode therein. Although the presently disclosed and/or claimed inventive concept(s) has been described in conjunction with the specific drawings, experimentation, results, and language set forth herein above, it is evident that many alternatives, modifications, and variations will be apparent to those of ordinary skill in the art. Accordingly, it is intended to embrace all such alternatives, modifications, and variations that fall within the spirit and broad scope of the presently disclosed and/or claimed inventive concept(s).

What is claimed is:

1. A fluid analyzer for analyzing a plurality of analytes present in biological fluid samples, the fluid analyzer comprising:
   a fluid channel;
   a potentiometric sensor for sensing a first analyte in a fluid sample, wherein the first analyte is magnesium, the potentiometric sensor comprising:
      a magnesium ion selective electrode in fluidic communication with the fluid channel;
      an interfering ion selective electrode in fluidic communication with the fluid channel, wherein the interfering ion selective electrode is a calcium ion selective electrode;
      a reference electrode in fluidic communication with the fluid channel;
   at least one additional sensor for sensing at least a second analyte in the fluid sample, the at least one additional sensor being in fluidic communication with the fluid channel;
   a meter receiving signals generated by the calcium ion selective electrode, the magnesium ion selective electrode, the reference electrode, and the at least one additional sensor and transforming the signals into information indicative of the electric potential of the first and second analytes;
   at least one calibration reagent injection port in fluidic communication with the fluid channel, the at least one calibration reagent injection port adapted to receive at least one predetermined calibration reagent;
   at least one automated valve positioned between the at least one calibration reagent injection port and the fluid channel, the at least one automated valve being openable and closable to provide one or more samples of the at least one predetermined calibration reagent to the fluid channel;
   a calibration cartridge in fluidic communication with the at least one calibration reagent injection port and comprising at least three calibration reagents, wherein each of the at least three calibration reagents has a magnesium ion concentration independently selected from a range of from about 0.1 mM to about 1.5 mM and a calcium ion concentration independently selected from a range of from about 0.2 mM to about 2.0 mM, wherein the at least three calibration reagents each comprise a different amount of magnesium ions and a different amount of calcium ions, and wherein at least one of the at least three calibration reagents is utilized with both the potentiometric sensor and the at least one additional sensor present in the fluid analyzer; and
   a control system having a processor executing processor executable code that causes the processor to:
      control the at least one automated valve to pass the at least three calibration reagents through the fluid channel to the potentiometric sensor and the at least one additional sensor and determine calibration information using calibration logic from signals generated by the meter, wherein the calibration information comprises a slope, an offset, and a selectivity coefficient;
      control the at least one automated valve to selectively pass different subsets of the at least three calibration reagents through the fluid channel to the potentiometric sensor and the at least one additional sensor and determine re-calibration information using the signals generated by the meter and at least one of the calibration information and re-calibration logic, wherein the re-calibration information comprises one or more of a slope, an offset, and a selectivity coefficient.

2. The fluid analyzer of claim 1, further comprising a sample injection port, whereby at a predetermined time the fluid sample is injected into the fluid channel.

3. The fluid analyzer of claim 2, wherein the fluid sample is manually injected into the fluid channel.

4. The fluid analyzer of claim 2, further comprising at least one automated sample valve positioned between the sample injection port and the fluid channel, the at least one automated sample valve being openable and closable to provide one or more samples of the fluid sample to the fluid channel.

5. The fluid analyzer of claim 4, wherein the processor of the control system executes processor executable code that causes the processor to control the at least one automated sample valve positioned between the sample injection port and the fluid channel to inject the fluid sample into the fluid channel.

6. The fluid analyzer of claim 1, wherein the subsets of the at least three calibration reagents may be selected from the group consisting of: (i) one of the at least three calibration reagents, (ii) two of the at least three calibration reagents, and (iii) all of the at least three calibration reagents.

7. The fluid analyzer of claim 1, further comprising:
   at least one quality control reagent injection port in fluidic communication with the fluid channel, the at least one quality control reagent inject ion port adapted to receive at least one predetermined quality control reagent consisting of magnesium aqueous solution; and
   at least one quality control automated valve positioned between the at least one quality control reagent port and the fluid channel, the at least one quality control automated valve being openable and closable to provide one or more samples of the at least one predetermined quality control reagent consisting of magnesium aqueous solution,
   wherein the control system comprises processor executable code that causes the processor to control the at least one automated quality control valve positioned between the at least one quality control reagent injection port and the fluid channel to pass the at least one predetermined quality control reagent consisting of magnesium aqueous solution through the fluid channel to the potentiometric sensor and the at least one additional sensor.

8. The fluid analyzer of claim 1, wherein the potentiometric sensor senses magnesium in the fluid sample at an accuracy level of about +/−1% throughout a use-life thereof of at least about 28 days.

9. The fluid analyzer of claim 1, wherein the at least one additional sensor comprises a potentiometric sensor for sensing an analyte selected from potassium ions, sodium ions, bicarbonate ions, and/or a pH level.

10. The fluid analyzer of claim 1, wherein the at least one additional sensor comprises an amphoteric sensor for sensing an analyte selected from partial oxygen pressure ($pO_2$), glucose, and/or lactate.

* * * * *